(12) United States Patent
Shimaoka et al.

(10) Patent No.: US 9,340,651 B2
(45) Date of Patent: May 17, 2016

(54) SUGAR CHAIN-CAPTURING SUBSTANCE AND USE THEREOF

(75) Inventors: Hideyuki Shimaoka, Tokyo (JP); Shinichiro Nishimura, Hokkaido (JP); Yasuro Shinohara, Hokkaido (JP); Yoshiaki Miura, Hokkaido (JP); Jun-ichi Furukawa, Hokkaido (JP)

(73) Assignees: Sumitomo Bakelite Company Limited, Tokyo (JP); National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 12/309,945

(22) PCT Filed: Aug. 6, 2007

(86) PCT No.: PCT/JP2007/000838
§ 371 (c)(1),
(2), (4) Date: Feb. 4, 2009

(87) PCT Pub. No.: WO2008/018170
PCT Pub. Date: Feb. 14, 2008

(65) Prior Publication Data
US 2009/0306291 A1 Dec. 10, 2009

(30) Foreign Application Priority Data
Aug. 9, 2006 (JP) ................................. 2006-217165

(51) Int. Cl.
C08G 63/91 (2006.01)
C08J 3/24 (2006.01)
C07C 233/20 (2006.01)
C07C 281/02 (2006.01)
C08F 8/30 (2006.01)
G01N 33/53 (2006.01)
C08F 122/38 (2006.01)
C07C 271/08 (2006.01)
C08F 222/10 (2006.01)
G01N 30/02 (2006.01)
G01N 30/88 (2006.01)

(52) U.S. Cl.
CPC ................. *C08J 3/24* (2013.01); *C07C 233/20* (2013.01); *C07C 271/08* (2013.01); *C07C 281/02* (2013.01); *C08F 8/30* (2013.01); *C08F 122/38* (2013.01); *G01N 33/5308* (2013.01); *C08F 2222/1013* (2013.01); *G01N 2030/027* (2013.01); *G01N 2030/8813* (2013.01); *G01N 2030/8836* (2013.01); *Y02P 20/55* (2015.11); *Y10T 428/2982* (2015.01)

(58) Field of Classification Search
CPC ........................................................ C08G 63/91
USPC ........................................................ 525/54.2
See application file for complete search history.

(56) References Cited

U.S. PATENT DOCUMENTS

| 2,918,493 A | 12/1959 | Panzer et al. |
| 3,783,136 A | 1/1974 | Inukai |
| 3,968,148 A | 7/1976 | Leister et al. |
| 5,612,203 A | 3/1997 | Maruo et al. |
| 5,668,272 A | 9/1997 | Prasad et al. |
| 6,218,546 B1 | 4/2001 | Watzele et al. |
| 7,964,687 B2 * | 6/2011 | Nishimura et al. ........... 526/304 |
| 2004/0023274 A1 | 2/2004 | Shinohara |
| 2004/0077812 A1 | 4/2004 | Okamoto et al. |
| 2005/0096360 A1 | 5/2005 | Salter-Cid et al. |
| 2005/0136001 A1 | 6/2005 | McBride et al. |
| 2006/0057099 A1 | 3/2006 | Ulbrich et al. |
| 2006/0188996 A1 * | 8/2006 | Nishimura et al. ............. 436/90 |
| 2008/0097061 A1 | 4/2008 | Nishimura et al. |
| 2008/0227092 A1 | 9/2008 | Lohse et al. |
| 2008/0254998 A1 | 10/2008 | Nishimura et al. |
| 2008/0318879 A1 | 12/2008 | Etrych et al. |

FOREIGN PATENT DOCUMENTS

| BD | 2006/025155 A1 | 3/2006 |
| DE | 19 60 716 A1 | 6/1971 |
| DE | 293 597 | 9/1991 |
| EP | 1 577 293 A1 | 9/2005 |
| GB | 933196 | 8/1963 |
| GB | 1 242 980 A | 8/1971 |
| JP | 62-146903 | 6/1987 |
| JP | 01-242070 | 9/1989 |
| JP | 08-059586 | 3/1996 |

(Continued)

OTHER PUBLICATIONS

"High-Throughput Protein Glycomics: Combined Use of Chemoselective Glycoblotting and MALDI-TOF/TOF Mass Spectomerty**" Nishimura et al. (Angew, Chem. Int. Ed. 2005, 44, 91-96.
Supplementary European Search Report for Application No. EP 07 79 0327 dated Feb. 26, 2010.
International Search Report, Mailed Oct. 23, 2007.
Yasuro Shinohara et al., "MALDI-TOF Kaiseki ni . . . Kaihatsu", Polymer Preprints, Japan, 2004 Nen, vol. S3, No. 2, pp. 5327-5328.
Noboru Yamazaki et al., "Kakushu Kinosei Zairyo eno Tosa Donyu Hoho", Preprints of Biotechnologhy Symposium, 1997 Nen, vol. 15, pp. 101-105.
Zhou X et al, "Oligosaccharide Microarrays Fabricated on Aminooxyacetyl Functionalized Glass Surface for Characterization of Carbohydrate-Protein Interaction", Biosensors and Bioelectronics, Elsevier BV, NL, vol. 21, No. 8, Feb. 15, 2006, pp. 1451-1458.
Shin et al., "Carbohydrate Microarrays: An Advanced Technology for Functional Studies of Glycans", Chemistry—A European Journal, Wiley- V C H Verlag GmbH & Co. KGaA, 2005, pp. 2894-2901.
Myung-Ryul Lee and Injae Shin: "Facile Preparation of Carbohydrate Microarrays by Site-Specific, Covalent Immobilization of Unmodified Carbohydrates on Hydrazide-Coated Glass Slides" Organic Letters, American Chemical Society, US vol. 7, No. 19, Sep. 15, 2005, pp. 4269-4272.

(Continued)

*Primary Examiner* — Yong Chu
*Assistant Examiner* — Sonya Wright
(74) *Attorney, Agent, or Firm* — Smith, Gambrell & Russell, LLP.

(57) ABSTRACT

The present invention provides a method for preparing a sample characterized by binding a substance A containing a hydrazide group to a sugar chain and/or a sugar derivative via hydrazone formation between the hydrazide group of the substance A and the reducing end of the sugar chain and/or the sugar derivative thereby to enable the separation and purification of the sugar chain and/or the sugar derivative for an analytical sample from a biological sample containing the sugar chain and/or the sugar derivative by a simple operation.

13 Claims, 8 Drawing Sheets

(56) References Cited

FOREIGN PATENT DOCUMENTS

| | | |
|---|---|---|
| JP | 09-235310 | 9/1997 |
| JP | 11-508564 | 7/1999 |
| JP | 2000-511949 | 9/2000 |
| JP | 2002-148805 | 5/2002 |
| JP | 2002-357901 | 12/2002 |
| JP | 2005-291958 | 10/2005 |
| SU | 412 189 A1 | 1/1974 |
| WO | 97/02277 | 1/1997 |
| WO | 97/42230 | 11/1997 |
| WO | 0239110 A2 | 5/2002 |
| WO | 02/088204 A1 | 11/2002 |
| WO | 03053473 A2 | 3/2003 |
| WO | 2004/058687 | 7/2004 |
| WO | 2005014530 A2 | 2/2005 |
| WO | 2005/097844 A1 | 10/2005 |
| WO | 2006/030584 | 3/2006 |
| WO | 2006/084461 A1 | 8/2006 |
| WO | 2007028347 A2 | 3/2007 |

OTHER PUBLICATIONS

Guillaumie Fetal: "Inmobilization of Pectin Fragments on Solid Supports: Novel Coupling by Thiazolidine Formation" Bioconjugate Chemistry, ACS, Washington, DC, US, vol. 13, Jan. 1, 2002, pp. 285-294.

Miquel Vila-Perello, Ricardo Gutierrez Gallego, David Andreu: "A Simple Approach to Well-Defined Sugar-Coated Surfaces for Interaction Studies", Chembiochem, vol. 6, No. 10, 2005, pp. 1831-1838.

Satoh Ayano et al: "Comparison of Methods of Immobilization to Enzyme-Linked Immuno Sorbent Assay Plates for the Detection of Sugar Chains" Analytical Biochemistry, Academic Press Inc, New York, vol. 275, No. 2, Nov. 15, 1999, pp. 231-235.

Nadkarni et al., "Directional Immobilization of Heparin Onto The Nonporous Surface of Polystyrene Microplates" Biotechniques, In Forma Heal Thcare, US, vol. 23, No. 3, Jan. 1, 1997, pp. 382-385.

Zhang et al., "Identification and Quantification of N-Linked Glycoproteins Using Hydrazide Chemistry, Stable Isotope Labeling and Mass Spectrometry" Nature Biotechnology, Nature Publishing Group, New York, NY, US, vol. 21, No. 6, Jun. 1, 2003, pp. 660-666.

Bilkova et al. "Oriented Immobilization of Chymotrypsin by use of Suitable Antibodies Coupled to a Non-porous Solid Support" Journal of Chromatography, Elsevier Science Publishers B.V, NL, vol. 852, No. 1, Aug. 6, 1999, pp. 141-149.

Snider et al: "Termination of Mn(III)—Based Oxidative Cyclizations by Trapping with Azide", Organic Letters, vol. 6, No. 8, 2004, pp. 1265-1268.

U. Heinz et al. "2-Tosyloxymethylcyclanones: Ring size Dependence of Fragmentation Versus Intramolecular Alkylation", Tetrahedron, vol. 46, No. 2, 12. 1990, pp. 4217-4230.

Chytil P et al. "Properties of HPMA Copolymer-Dexorubicin Conjugates with pH-controlled Activation Effect of Polymer Chain Modification" Journal of Controlled Release, Elsevier, Amsterdam, NL vol. 115, No. 1, Jun. 30, 2006, pp. 26-36.

Ulbrich K. et al. "Antibody-targeted polymer-doxorubicin conjugates with pH-controlled activation", Journal of Drug Targeting Harwood Academic Publishers GMBH, DE vol. 12, No. 8, 2004, pp. 447-489.

Lattova E et al: "Labelling Saccharides with Phenylhydrazine for Electrospray and Matrix-Assisted Laser Desorption-ionization Mass Spectrometry", Journal of Chromatography B: Biomedical Sciences & Applications, vol. 793, No. 1, Aug. 5, 2003.

Zhou et al.: "Assignment of Absolute Stereochemistry of Aminopolyols by the Bichromophoric Excition Chirality Method", J. Chem. Soc., Chem Commun., 1991, pp. 256-258.

Hao Wang et al. "A General Method for Producing Bioaffinity MALDI Probes", Analytical Chemistry, vol. 71. No. 10, 1999, pp. 2014-2020.

El Ashry E S H et al: Reaction of Sugars with 2-hydrazinopryidine, Precursors for Seco C-Nucleosides of Database BIOSIS (Online), Biosciences Information Services, Philadelphia, PA, US, Mar. 2004.

Bendiak et al.: "Sequential Removal of Monosaccharides form the Reducing Endof Oligosaccharides. 2. Fundamental Studies of a Reaction between Hydrazino Compounds and Sugars Having a Carbon Atom Adjacent to a Carbonyl Group", J. Org. Chem., vol. 60, 1995, pp. 8245-8256.

Stroh, et al., "Zur Kondensationvon Carbonylverbindungen mit Hydrazinen, XIII: Uber die Reaktion von Alkyl—und Aralkylhydrazinen mit Zuckern", Chem. Ber., vol. 98, 1965, pp. 1588-1597.

Helferich, B. et al., "Zuckersynthesen V. Die Synthese einiger Trisaccharide", Justus Liebigs Ann. Chem., vol. 450, 1926, p. 229-237.

R. Seka et al., "Zur Kenntnis der Kondensationsprodukte des Phenylessigaurehydrazids", Monatshefte Fur Chemie Und Verwandte Teile Anderer Wissenschaften, vol. 57, 1931, pp. 45-51.

Roberts, et al., "Determination of the Viscometric Constants for Chitosan", International Journal of Biological Macromolecules, vol. 4, No. 6., 1982, pp. 374-377.

Lattova et al., "Matrix-assisted Laser desorption/ionization tandem mass spectrometry and post-source decay fragmentation study of phenylhydrazones of N-linked oligosaccharides from ovalbumin", Journal of the Amercan Society for Mass Spectrometry, vol. 15, No. 5, 2004, pp. 725-735.

Goswami et al., "A Novel one-pot two-component synthesis of tricyclic pyrano [2,3-b] quinoxalines", Tetrahedron Letters, vol. 46., No. 2, Jan. 10, 2005, pp. 221-224.

Y. Shinohara et al. "Direct N-Glycan Profiling in the resence of Tryptic Pettides on MALDI-TDF by Controlled Ion Enhancement and Suppression upon Glycan-Selective Derivatization", Analytical Chemistry, vol. 76, No. 23, 2004, pp. 6989-6997.

Avigad et al., "Dansyl Hydrazine as a Fluorimetric Reagent for Thin-Layer Chromatographic Analysis of Reducing Sugars", Journal of Chromatography, Elsevier Science Publishers B.V. NL, vol. 139, No. 2, 21 Sep. 1997, pp. 343-347.

Zhang et al., "Synthesis and Application of Fmoc-hydrazine for the quantitative determination of saccharides by reversed-phase high performance liquid chromatography in the low and subpicomole range", Analytical Biochemistry, Academic Press Inc., New Yor, vol. 195, No. 1, May 15, 1991.

Extended European Search Report for counterpart application No. 12004569.5, dated Oct. 15, 2013 (claims included).

Extended European Search Report for counterpart application No. 12004558.7, dated Oct. 18, 2013 (claims included).

Extended European Search Report for counterpart application No. 12004570.3, dated Oct. 28, 2013 (claims included).

Hideyuki Shimaoka "Synthesis and Evaluation of Glyco-Blotting Polymer Particle—A New Methodology of High-troughput Glycopatterinlng)"; Polymer Preprints, Japan, vol. 53, No. 2, Sep. 1, 2004. pp. 5376-5377 (With English Abstract).

Shimaoka et al., "Development of S-Bio Blot Glyco, a Versatile Kit for High—throughput Oligosaccharide Purification Via Chemoselective Glycoblotting"; Bio Industry, vol. 22, No. 11 2005, pp. 54-59. (With English Abstract).

Office Action for JP 2008-528715 dated Feb. 28,2013.
Office Action for JP 2012-103020 dated Mar. 19, 2013.
Office Action for JP 2012-103021 dated Mar. 19, 2013.
Office Action for JP 2012-103024 dated Mar. 19, 2013.
Office Action for JP 2012-103025 dated Mar. 19, 2013.
Office Action for JP 2012-103027 dated Mar. 7, 2013.

* cited by examiner

Reaction of 2-hydrazinopyridine with sugar chain

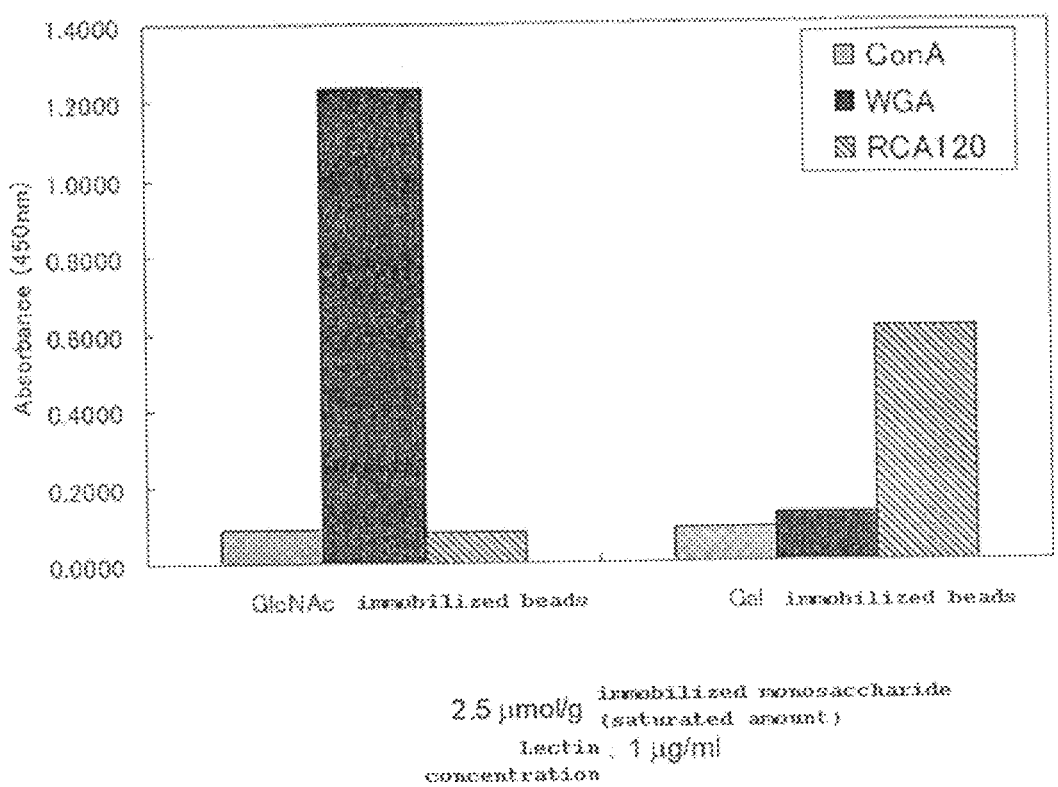

Fig. 9

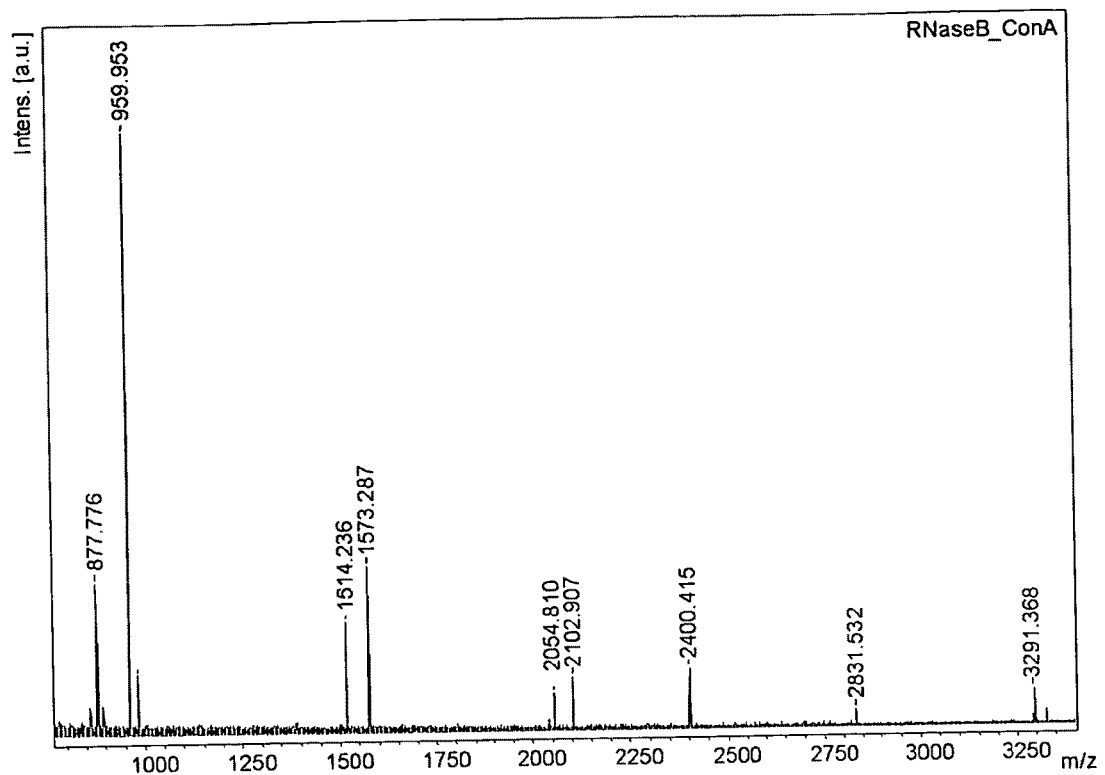

| m/z obsbd. | Estimated peptide sequence | Calcd. peptide mass | Origin |
|---|---|---|---|
| 877.776 | WNMQNGK | 877.398 | Con A (Jack bean, brazilian jack bean) |
| 959.953 | LLGLFPDAN | 959.519 | Con A (Brazilian jack bean) |
| 1514.236 | ETNTILSWSFTSK | 1513.753 | Con A (Jack bean, brazilian jack bean) |
| 1573.287 | VGTAHIIYNSVDKR | 1572.849 | Con A (Jack Bean) |
| 2054.81 | Artifact | | |
| 2102.907 | DLILQGDATTGTDGNLELTR | 2103.056 | Con A (Jack Bean) |
| 2400.415 | Artifact | | |
| 2831.532 | SPDSHPADGIAFFISNIDSSIPSGSTGR | 232.343 | Con A (Jack bean, brazilian jack bean) |
| 3291.368 | LSAVVSYPNADSATVSYDVDLDNVLPEWVR | 3294.616 | Con A (Jack Bean) | ized
SUGAR CHAIN-CAPTURING SUBSTANCE AND USE THEREOF

TECHNICAL FIELD

The present invention relates to a method for preparing a sample using a prescribed sugar chain-capturing substance, and an analytical sample obtained by the method. The present invention relates to a method for preparing a sugar chain-capturing substance, a compound used for the method and a polymer obtained by polymerizing the compound. Further, the present invention relates to the use of the sugar chain-capturing substance, for example, a method for applying the sugar-chain capturing substance, a sugar chain microarray, the use of the sugar chain microarray, sugar chain affinity beads and the use of the sugar chain affinity beads.

BACKGROUND ART

A biological polymer refers to a general term of a sugar chain, glycoprotein, glycopeptide, peptide, oligopeptide, protein, nucleic acid, lipid or the like.

Furthermore, these biological polymers play an importance role in biotechnology fields such as medical science, cell engineering, organs and medical engineering and the like. To clarify the control mechanism of the biological reaction using these substances is related to the development in the biotechnology fields.

Of these biological polymers, a sugar chain is extremely rich in its diversity, and is a substance participating in various functions of an organism present in the nature. The sugar chain is present as glycoconjugate bonded to protein, lipid or the like in vivo in many cases, and is one of important components in vivo. It has become clear that the sugar chain in vivo is deeply related to information transfer between cells, regulation of functions or interaction of protein, and the like.

Incidentally, the term "sugar chain" refers to a generic term of a chain of molecules coupled with monosaccharide such as glucose, galactose, mannose, fucose, xylose, N-acetylglucosamine, N-acetylgalactosamine, sialic acid or the like and a derivative thereof by a glycosidic bond.

Examples of the biological polymer having a sugar chain include proteoglycan of a cell wall of a plant cell contributing to the stability of cells, glycolipid affecting cell differentiation, population growth, adhesion, migration or the like, glycoprotein taking part in intercellular interaction or cellular recognition and the like. A mechanism of the sugar chain contained in these biological polymers of controlling a high-precision biological reaction while acting for, helping, amplifying, regulating or hindering functions mutually with the biological polymer has been gradually made clear. Furthermore, when the relationship between such a sugar chain and cell differentiation, population growth, cell adhesion, immunity and a malignant change (cancer) in cells becomes clear, a new development can be expected to be planned by closely relating this sugar chain engineering to the medical science, cell engineering or organs and medical engineering.

In Patent Document 1, there have been described a substance capable of specifically reacting with such a sugar chain and a method of separating a sugar chain by using the substance as well.

Patent Document 1: International Publication Pamphlet No. 2004/058687

DISCLOSURE OF THE INVENTION

By the way, in Patent Document 1, there has been described an example using an acid treatment employing trifluoroacetic acid, acidic resin or the like in order to release (excise) the sugar chain captured by using a sugar chain-capturing substance from the sugar chain-capturing substance. To expose the sugar chain under such severe conditions may cause degeneration of the sugar chain such as separation of a sialic acid residue having a property of being bonded to a terminal end of the sugar chain that is taken out from a biological sample and a property of being easily separated under acidic conditions. So, it has been demanded that excision of the sugar chain is carried out under much milder conditions. Incidentally, the existence of the sialic acid to be bonded to the sugar chain and the binding site are related to diseases in many cases so that it has been demanded that the sugar chain is analyzed in the perfect state of the sialic acid. When even a part of the sialic acid is separated at the pre-treatment step before analysis, accurate information of the sugar chain cannot be obtained.

Then, the present invention is to provide a method for preparing a sample which enables the separation and purification of the sugar chain and/or the sugar derivative for an analytical sample from a biological sample containing a sugar chain and/or a sugar derivative by a simple operation, and an analytical sample obtained by this method. Furthermore, the present invention is to provide a method for preparing a sugar chain-capturing substance which is used in the aforementioned method for preparing a sample, a monomer which can be used for the preparation method, and a polymer obtained by polymerizing this monomer. Further, the present invention is to provide the use of the aforementioned method for preparing a sample.

The present invention provides:

(1) a method for preparing a sample in which a substance A containing a hydrazide group is bonded to a sugar chain and/or a sugar derivative via hydrazone formation between the hydrazide group of the substance A and the reducing end of the sugar chain and/or the sugar derivative;

(2) the method for preparing a sample as set forth in (1), in which the substance A includes a moiety containing chromophore or fluorophore;

(3) the method for preparing a sample as set forth in (1), in which the substance A is a substance selected from the following substances or a salt thereof, (substance A): 5-Dimethylaminonaphthalene-1-sulfonyl hydrazine (Dansylhydrazine); 2-hydrazinopyridine; 9-fluorenylmethyl carbazate (Fmoc hydrazine); benzylhydrazine; 4,4-difluoro-5,7-dimethyl-4-bora-3a,4a-diaza-s-indacene-3-propionic acid, hydrazide; 2-(6,8-difluoro-7-hydroxy-4-methylcoumarin)acetohydrazide; 7-diethylaminocoumarin-3-carboxylic acid, hydrazide (DCCH); phenylhydrazine; 1-Naphthaleneacethydrazide; 2-hydrazinobenzoic acid; biotin hydrazide; and phenylacetic hydrazide;

(4) the method for preparing a sample as set forth in (1), in which the substance A contains a moiety consisting of at least one of an arginine residue, a tryptophan residue, a phenylalanine residue, a tyrosine residue, a cysteine residue and a derivative thereof;

(5) the method for preparing a sample as set forth in (4), in which the substance A is a compound having a structure of the following formula (1),

[Chemical Formula 1]

(Formula 1)

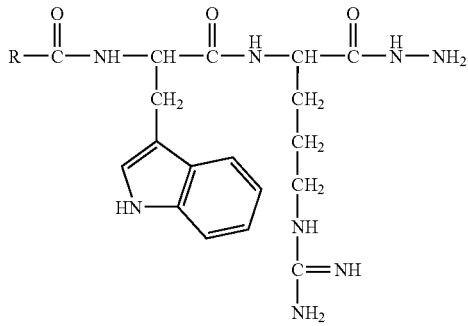

wherein, in the formula, R represents —$CH_3$ or —$CD_3$;

(6) the method for preparing a sample as set forth in (1), in which the substance A has a structure of the following formula (2),

[Chemical Formula 2]

(Formula 2)

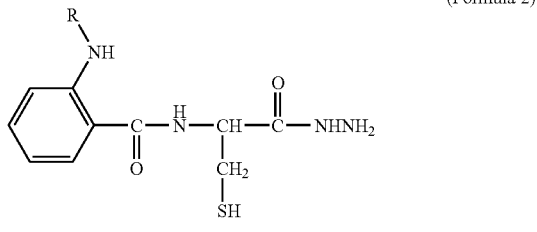

wherein, in the formula, R represents any of H, —$COCH_3$ or —$COCD_3$;

(7) the method for preparing a sample as set forth in (1), in which the substance A is represented by the following formula (3),

[Chemical Formula 3]

(carrier)-R—$NHNH_2$ (Formula 3)

wherein, in the formula, the carrier represents a polymer matrix; and R represents a hydrocarbon chain having 1 to 20 carbon atoms which may be interrupted with —O—, —S—, —NH—, —CO— or —CONH—;

(8) the method for preparing a sample as set forth in (7), in which the substance A has a crosslinked polymer structure represented by the following formula (4),

[Chemical Formula 4]

(Formula 4)

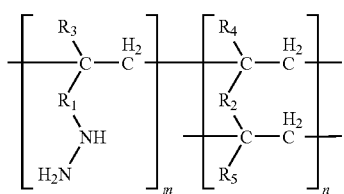

wherein, in the formula, $R_1$ and $R_2$ represent a hydrocarbon chain having 1 to 20 carbon atoms which may be interrupted with —O—, —S—, —NH—, —CO— or —CONH—; $R_3$, $R_4$ and $R_5$ represent H, $CH_3$ or a hydrocarbon chain having 2 to 5 carbon atoms; and m and n represent the number of monomer units;

(9) the method for preparing a sample as set forth in (7), in which the substance A has a crosslinked polymer structure represented by the following formula (5),

[Chemical Formula 5]

(Formula 5)

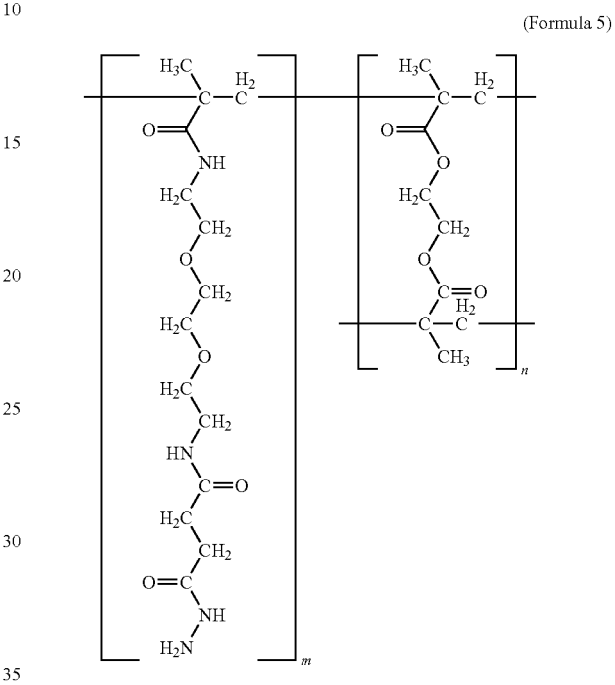

wherein, in the formula, m and n represent the number of monomer units;

(10) the method for preparing a sample as set forth in any one of (7) to (9), in which the substance A is a polymer particle having an average particle diameter of equal to or more than 0.1 and equal to or less than 500 μm;

11) the method for preparing a sample as set forth in any one of (7) to (10), in which the substance A is a polymer particle having a hydrazide group of a dry weight of not less than 100 nmol per 1 mg;

(12) the method for preparing a sample as set forth in any one of (7) to (10), in which the substance A is a polymer particle having a hydrazide group of a dry weight of not less than 0.5 μmol per 1 mg;

(13) the method for preparing a sample as set forth in any one of (7) to (12), in which the substance A is stable at the pH of 3 to 8;

(14) the method for preparing a sample as set forth in any one of (7) to (12), in which the substance A is stable under pressure of at least not more than 1 MPa;

(15) the method for preparing a sample as set forth in (7), in which the carrier in the above formula (3) is a substance to be directly bonded to a solid phase substrate or a surface of the solid phase substrate;

(16) a method for preparing a sample which involves the sugar chain capture step including binding a substance A to a sugar chain and/or a sugar derivative according to the method for preparing a sample as set forth in any one of (1) to (15); and the sugar chain release step including the action of a substance B containing an aminooxy group or a hydrazide group on a complex of the substance A and the sugar chain and/or the sugar derivative, captured in the sugar chain capture step and binding the sugar chain and/or the sugar derivative while cut off from the substance A to the substance B in accordance with the hydrazone-oxime exchange reaction or the hydrazone-hydrazone exchange reaction occurred between the complex and the substance B;

(17) the method for preparing a sample as set forth in (16), in which the substance B includes a moiety containing chromophore or fluorophore;

(18) the method for preparing a sample as set forth in (16), in which the substance B is a substance selected from the group consisting of the following substances containing a hydrazide group or the following substances containing an aminooxy group or a salt, (Substances containing a hydrazide group) 5-Dimethylaminonaphthalene-1-sulfonyl hydrazine (Dansylhydrazine); 2-hydrazinopyridine; 9-fluorenylmethyl carbazate (Fmoc hydrazine); benzylhydrazine; 4,4-difluoro-5,7-dimethyl-4-bora-3a,4a-diaza-s-indacene-3-propionic acid, hydrazide; 2-(6,8-difluoro-7-hydroxy-4-methylcoumarin)acetohydrazide; 7-diethylaminocoumarin-3-carboxylic acid, hydrazide (DCCH); phenylhydrazine; 1-Naphthaleneacethydrazide; 2-hydrazinobenzoic acid; and phenylacetic hydrazide; or (Substances containing an aminooxy group) O-benzylhydroxylamine; O-phenylhydroxylamine; O-(2,3,4,5,6-pentafluorobenzyl)hydroxylamine; O-(4-nitrobenzyl)hydroxylamine; 2-aminooxypyridine; 2-aminooxymethylpyridine; 4-[(aminooxyacetyl)amino]benzoic acid methyl ester; 4-[(aminooxyacetyl)amino]benzoic acid ethyl ester; and 4-[(aminooxyacetyl)amino]benzoic acid n-butyl ester;

(19) the method for preparing a sample as set forth in (16), in which the substance B contains a moiety consisting of at least one of an arginine residue, a tryptophan residue, a phenylalanine residue, a tyrosine residue, a cysteine residue and a derivative thereof;

(20) the method for preparing a sample as set forth in (16), in which the substance B has a structure represented by the following formula (7),

[Chemical Formula 6]

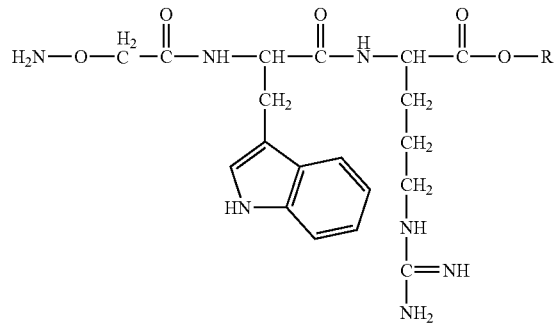

(Formula 7)

wherein, in the structural formula, R represents —CH$_3$ or —CD$_3$;

(21) the method for preparing a sample as set forth in (16), in which the substance B is a solid phase carrier;

(22) the method for preparing a sample as set forth in (21), in which the substance B is a solid phase carrier containing an aminooxy group;

(23) the method for preparing a sample as set forth in (22), in which the substance B is represented by the following formula (12),

[Chemical Formula 7]

(Carrier)-R—ONH$_2$     (Formula 12)

wherein, in the formula, the carrier represents a polymer matrix; and R represents a hydrocarbon chain having 1 to 20 carbon atoms which may be interrupted with —O—, —S—, —NH—, —CO— or —CONH—;

(24) the method for preparing a sample as set forth in (23), in which the substance B is a polymer particle having a structure represented by the following formula (8),

[Chemical Formula 8]

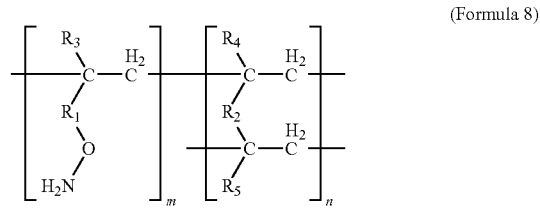

(Formula 8)

wherein, in the formula, R$_1$ and R$_2$ represent a hydrocarbon chain having 1 to 20 carbon atoms which may be interrupted with —O—, —S—, —NH—, —CO— or —CONH—; R$_3$, R$_4$ and R$_5$ represent H, CH$_3$ or a hydrocarbon chain having 2 to 5 carbon atoms; and m and n represent the number of monomer units;

(25) the method for preparing a sample as set forth in (23), in which the substance B is a polymer particle having a structure represented by the following formula (9),

[Chemical Formula 9]

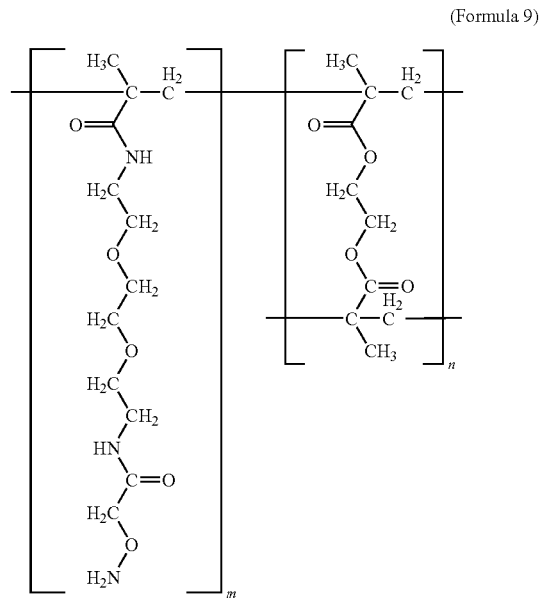

(Formula 9)

wherein, in the formula, m and n represent the number of monomer units;

(26) the method for preparing a sample as set forth in (21), in which the solid phase carrier is a substance to be directly bonded to a solid phase substrate or a surface of the solid phase substrate;

(27) the method for preparing a sample as set forth in any one of (16) to (25), in which the hydrazone-oxime exchange reaction or the hydrazone-hydrazone exchange reaction is carried out at least one or more times after the completion of the sugar chain release step;

(28) a method for preparing a sample in which a hydrazone bond is dissociated and a sugar chain and/or a sugar derivative is released by treating a substance A having a structure represented by the following formula (3), (4) or (5) under acidic conditions to which the sugar chain and/or the sugar derivative is bonded,

[Chemical Formula 10]

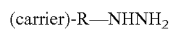

(carrier)-R—NHNH$_2$ (Formula 3)

wherein, in the formula, the carrier represents a polymer matrix; and R represents a hydrocarbon chain having 1 to 20 carbon atoms which may be interrupted with —O—, —S—, —NH—, —CO— or —CONH—,

[Chemical Formula 11]

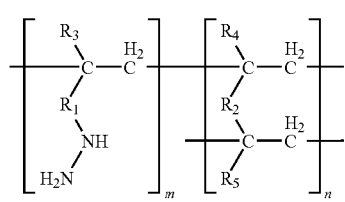

(Formula 4)

wherein, in the formula, R$_1$ and R$_2$ represent a hydrocarbon chain having 1 to 20 carbon atoms which may be interrupted with —O—, —S—, —NH—, —CO— or —CONH—; R$_3$, R$_4$ and R$_5$ represent H, CH$_3$ or a hydrocarbon chain having 2 to 5 carbon atoms; and m and n represent the number of monomer units,

[Chemical Formula 12]

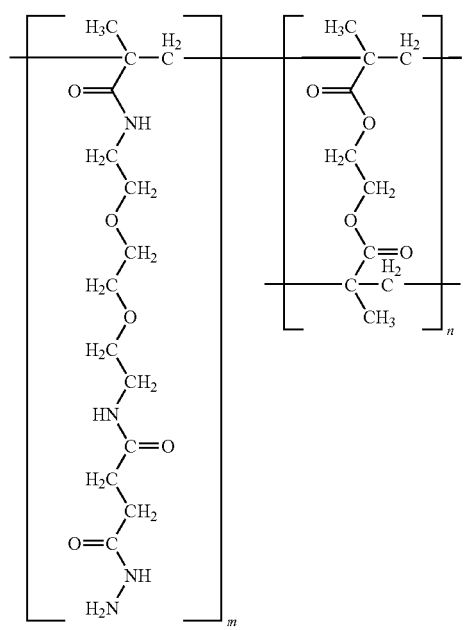

(Formula 5)

wherein, in the formula, m and n represent the number of monomer units;

(29) the method for preparing a sample as set forth in (28), in which the treatment under acidic conditions is carried out using a trifluoroacetic acid solution of 0.01 to 10 volume percentage;

(30) the method for preparing a sample as set forth in (29), in which the treatment under acidic conditions is carried out using a trifluoroacetic acid solution of 0.01 to 1 volume percentage at 25 to 80 degree centigrade for 5 to 60 minutes;

(31) an analytical sample prepared by the method for preparing a sample as set forth in any one of (1) to (30);

(32) a method for preparing a substance A represented by the following formula (3), in which a polymer particle containing carboxylic acid ester is obtained by polymerizing a raw material containing a carboxylic acid ester monomer having a polymerizable group in the presence of a crosslinking agent, and then the polymer particle containing carboxylic acid ester is treated with a hydrazine solution of a concentration of not less than 10 volume percentage,

[Chemical Formula 13]

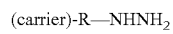

(carrier)-R—NHNH$_2$ (Formula 3)

wherein, in the formula, the carrier represents a polymer matrix; and R represents a hydrocarbon chain having 1 to 20 carbon atoms which may be interrupted with —O—, —S—, —NH—, —CO— or —CONH—;

(33) the method for preparing a substance A as set forth in (32), in which the carboxylic acid ester monomer is carboxylic acid methyl ester;

(34) a monomer having a structure represented by the following formula (10),

[Chemical Formula 14]

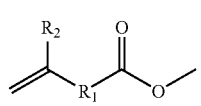

(Formula 10)

wherein, in the formula, R$_1$ represents a hydrocarbon chain having 1 to 20 carbon atoms which may be interrupted with —O—, —S—, —NH—, —CO— or —CONH—; and R$_2$ represents H, CH$_3$ or a hydrocarbon chain having 2 to 5 carbon atoms;

(35) a polymer obtained by polymerizing the monomer as set forth in (34);

(36) a monomer having a structure represented by the following formula (11),

[Chemical Formula 15]

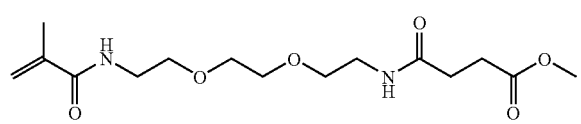

(Formula 11)

(37) a polymer obtained by polymerizing the monomer as set forth in (36);

(38) a monomer having a structure represented by the following formula (13),

[Chemical Formula 16]

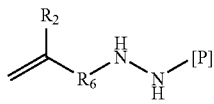

(Formula 13)

wherein, in the formula, $R_2$ represents H, $CH_3$ or a hydrocarbon chain having 2 to 5 carbon atoms; $R_6$ represents a hydrocarbon chain having 1 to 20 carbon atoms which may be interrupted with —O—, —S—, —NH—, —CO— or —CONH—; and [P] represents a protective group;

(39) a polymer obtained by polymerizing the monomer as set forth in (38);

(40) the polymer as set forth in (39), obtained by subjecting the protective group [P] of the formula (13) to deprotection by the acid treatment;

(41) a monomer having a structure represented by the following formula (14),

[Chemical Formula 17]

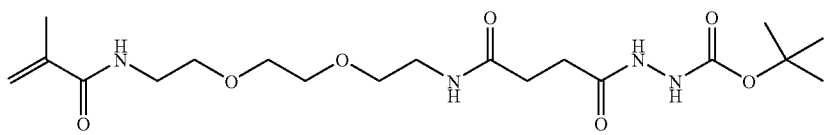

(Formula 14)

(42) a polymer obtained by polymerizing the monomer as set forth in (41);

(43) a polymer obtained by subjecting a t-butoxycarbonyl group of the polymer as set forth in (42) to deprotection by the acid treatment;

(44) a method for preparing a substance A represented by the following formula (4), in which a polymer particle containing carboxylic acid ester is obtained by polymerizing a monomer having a structure of the following formula (10) in the presence of a crosslinking agent, and then the polymer particle containing carboxylic acid ester is treated with a hydrazine solution of a concentration of not less than 10 volume percentage,

[Chemical Formula 18]

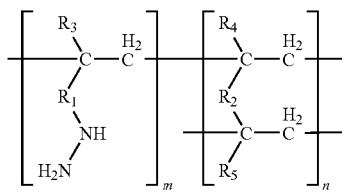

(Formula 4)

wherein, in the formula, $R_1$ and $R_2$ represent a hydrocarbon chain having 1 to 20 carbon atoms which may be interrupted with —O—, —S—, —NH—, —CO— or —CONH—; $R_3$, $R_4$ and $R_5$ represent H, $CH_3$ or a hydrocarbon chain having 2 to 5 carbon atoms; and m and n represent the number of monomer units,

[Chemical Formula 19]

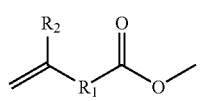

(Formula 10)

wherein, in the formula, $R_1$ represents a hydrocarbon chain having 1 to 20 carbon atoms which may be interrupted with —O—, —S—, —NH—, —CO— or —CONH—; and $R_2$ represents H, $CH_3$ or a hydrocarbon chain having 2 to 5 carbon atoms;

(45) a method for preparing a substance A represented by the following formula (5), in which a polymer particle containing carboxylic acid ester is obtained by polymerizing a monomer having a structure of the following formula (11) in the presence of a crosslinking agent, and then the polymer particle containing carboxylic acid ester is treated with a hydrazine solution of a concentration of not less than 10 volume percentage,

[Chemical Formula 20]

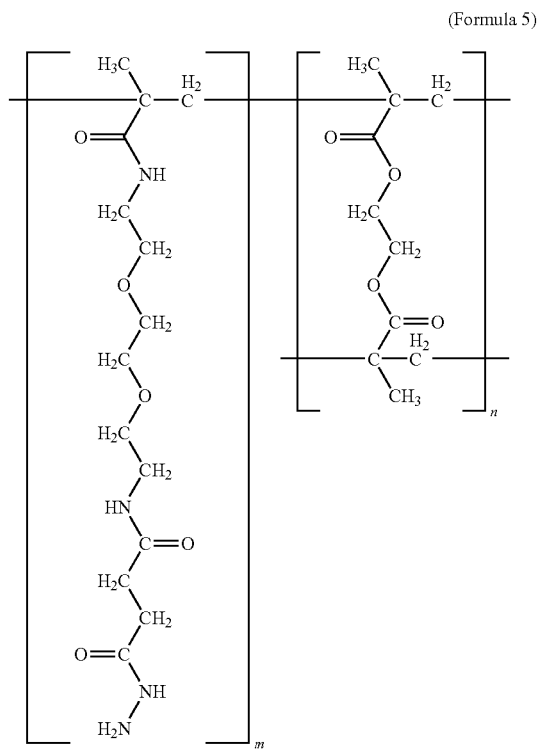

(Formula 5)

wherein, in the formula, m and n represent the number of monomer units,

[Chemical Formula 21]

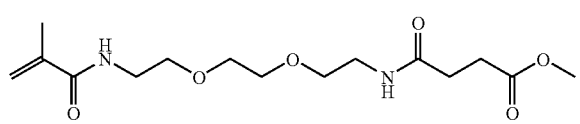

(Formula 11)

(46) a method of applying a solid phase carrier onto which a sugar chain and/or a sugar derivative obtained by subjecting a mixture or a specific fraction from the mixture to the isolation and purification is immobilized as a carrier for collecting a substance having a bonding property or affinity to the sugar chain and/or the sugar derivative;

(47) a method for preparing a sugar chain microarray, in which a sugar chain and/or a sugar derivative is immobilized onto a surface of a solid phase substrate composed of a solid phase carrier including a substance B having a structure represented by the following formula (3) or (12) according to the following steps (1) to (4), (step 1) a step of purifying and/or isolating the sugar chain and/or the sugar derivative by a specific separation means by binding the sugar chain and/or the sugar derivative to a compound containing a soluble hydrazide group, (step 2) a step of dispensing drops of a solution of the compound obtained in the step (1) in a row onto the solid phase substrate, (step 3) a step of proceeding a reaction of exchanging a sugar chain-substance A bond with a solid phase substrate-sugar chain bond by incubating the solid phase substrate after the completion of dispensing drops under prescribed conditions, and immobilizing the sugar chain and/or the sugar derivative onto the solid phase substrate, and (step 4) a step of washing and removing the unreacted substance on the solid phase substrate,

[Chemical Formula 22]

(Carrier)-R—NHNH$_2$  (Formula 3)

wherein, in the formula, the carrier represents a polymer matrix; and R represents a hydrocarbon chain having 1 to 20 carbon atoms which may be interrupted with —O—, —S—, —NH—, —CO— or —CONH—,

[Chemical Formula 23]

(Carrier)-R—ONH$_2$  (Formula 12)

wherein, in the formula, the carrier represents a polymer matrix; and R represents a hydrocarbon chain having 1 to 20 carbon atoms which may be interrupted with —O—, —S—, —NH—, —CO— or —CONH—;

(48) a sugar chain microarray produced by the method as set forth in (47);

(49) a system for searching a sugar-binding substance for specifically binding to or adsorbing the immobilized sugar chain and/or the immobilized sugar derivative by bringing a solution containing a specimen into contact with a surface of the sugar chain microarray as set forth in (48), incubating and washing under prescribed conditions, and then detecting the sugar-binding substance collected at the sugar chain and/or the sugar derivative of a drop-dispensed portion on the solid phase substrate;

(50) a system for evaluating the recognition specificity of a binding protein by bringing a solution containing a specimen into contact with a surface of the sugar chain microarray as set forth in (48), collecting a sugar binding protein in the specimen at the sugar chain and/or the sugar derivative of a drop-dispersed region on the solid phase substrate, and quantitatively analyzing the collected amount by a prescribed quantifying means;

(51) a method for preparing sugar chain affinity beads, in which a sugar chain and/or a sugar derivative is immobilized onto a surface of the polymer composed of a solid phase carrier including a substance B having a structure represented by the following formula (3) or (12),

[Chemical Formula 24]

(Carrier)-R-NHNH$_2$  (Formula 3)

wherein, in the formula, the carrier represents a polymer matrix; and R represents a hydrocarbon chain having 1 to 20 carbon atoms which may be interrupted with —O—, —S—, —NH—, —CO— or —CONH—,

[Chemical Formula 25]

(Carrier)-R—ONH$_2$  (Formula 12)

wherein, in the formula, the carrier represents a polymer matrix; and R represents a hydrocarbon chain having 1 to 20 carbon atoms which may be interrupted with —O—, —S—, —NH—, —CO— or —CONH—;

(52) the method for preparing sugar chain affinity beads as set forth in (51), in which the sugar chain and/or the sugar derivative is immobilized onto a surface of the polymer particle according to the following steps (1) to (3), (step 1) a step of purifying and/or isolating the sugar chain and/or the sugar derivative by a specific separation means by binding the sugar chain and/or the sugar derivative to a compound containing a soluble hydrazide group, (step 2) a step of immobilizing the sugar chain and/or the sugar derivative onto the polymer particle by bringing the compound obtained in the step (1) into contact with the polymer particle and incubating under prescribed conditions for exchanging a sugar chain-hydrazide group-containing compound bond with a sugar chain-polymer particle bond, and (step 3) a step of washing and removing the unreacted substance on the polymer particle;

(53) sugar chain affinity beads prepared by the method as set forth in (51) or (52); and

(54) a system for bringing a solution containing a specimen into contact with the sugar chain affinity beads as set forth in (53), incubating under prescribed conditions and washing, and then isolating the captured sugar-binding substance.

According to the present invention, a sugar chain and/or a sugar derivative for an analytical sample is enabled to be separated and purified from a biological sample containing the sugar chain and/or the sugar derivative by a simple operation.

BRIEF DESCRIPTION OF THE DRAWINGS

The above and other objects, features and advantages will be apparent from the following detailed description of the preferred embodiments in conjunction with the accompanying drawings.

FIG. 8 is a graph illustrating the verification results of a lectin capturing ability of Experimental Example 9(2). The vertical axis indicates the absorbance at 450 nm. The lectin concentration is 1 µg/ml, and the mole number of lectin immobilized onto monosaccharide is 2.5 µmol/g (saturated amount).

FIG. 9 is a graph illustrating the verification results of a lectin capturing ability of Experimental Example 10(2). The horizontal axis represents the molecular weight (m/z), while the vertical axis represents the intensity.

BEST MODE FOR CARRYING OUT THE INVENTION

Figure 1:
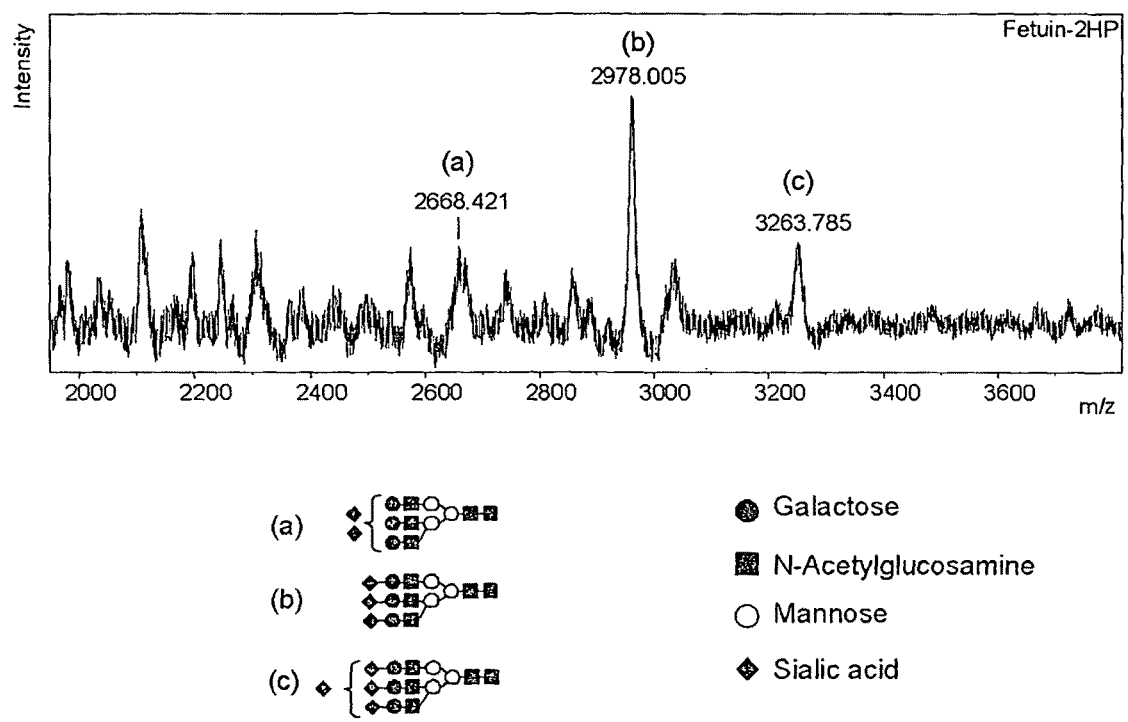
FIG. 1 illustrates a MALDI-TOF-MS chart of the reactant of a sugar chain and 2-hydrazinopyridine. The horizontal axis represents the molecular weight (m/z), while the vertical axis represents the intensity. Furthermore, structures of the sugar chain expected at a peak (a) in 2668.421 (=m/z), a peak (b) in 2978.005 (=m/z) and a peak (c) in 3263.785 are schematically represented by ●: galactose, ■: N-acetylglucosamine, ○: mannose and ◆: sialic acid.

Embodiments of the present invention will be described below.

From one of viewpoints, the present invention provides a method for preparing a sample characterized by binding a substance A containing a hydrazide group to a sugar chain and/or a sugar derivative via hydrazone formation between the hydrazide group of the substance A and the reducing end of the sugar chain and/or the sugar derivative.

The substance A containing a hydrazide group used in the method for preparing a sample is not particularly limited as long as it contains a hydrazide group (—NHNH—) at the end part. This hydrazide group is reacted with an aldehyde group for forming a specific and stable bonding in an equilibrium between the cyclic hemiacetal type and the non-cyclic aldehyde type formed by the sugar chain in a solution such as an aqueous solution or the like, thereby enabling to capture the sugar chain. Herein, the sugar chain capture reaction refers to a reaction as illustrated below,

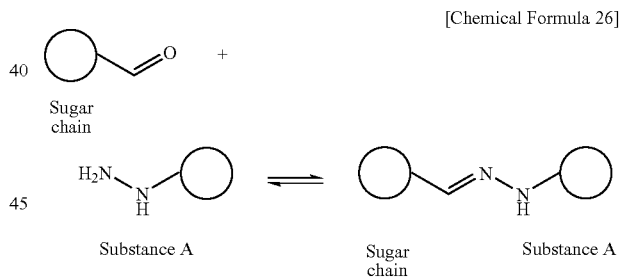

[Chemical Formula 26]

Herein, the substance A may be in the form of either a low-molecular compound or a solid phase carrier.

When a low-molecular compound is used, it is preferable that the substance A contains a moiety consisting of at least one of an arginine residue, a tryptophan residue, a phenylalanine residue, a tyrosine residue, a cysteine residue and a derivative thereof from the following viewpoints.

That is, when the substance A contains an arginine (R) residue, there have been known that the ionization is accelerated at the time of measurement of MALDI-TOF-MS, and the detection sensitivity is improved. Furthermore, from the fact that tryptophan (W) is a fluorescent amino acid and is hydrophobic, improvement in the isolation by the reverse phase HPLC and improvement in the fluorescence detection sensitivity can be attempted. Incidentally, when phenylalanine (F) and tyrosine (Y) are used, such a sample is suitable for detection by UV absorption.

Further, when cysteine is used, the substance A containing cysteine can be bonded to other substance containing a —SH group by an S—S bond using a thiol group in a side chain. For example, such a substance A can be immobilized onto the solid phase carrier containing a —SH group. Further, as other example, such a substance A can be used for the ICAT method (Isotope-Coded Affinity Tags).

As an example of such a substance A, a compound having a structure of the following formula (1) can be cited,

[Chemical Formula 27]

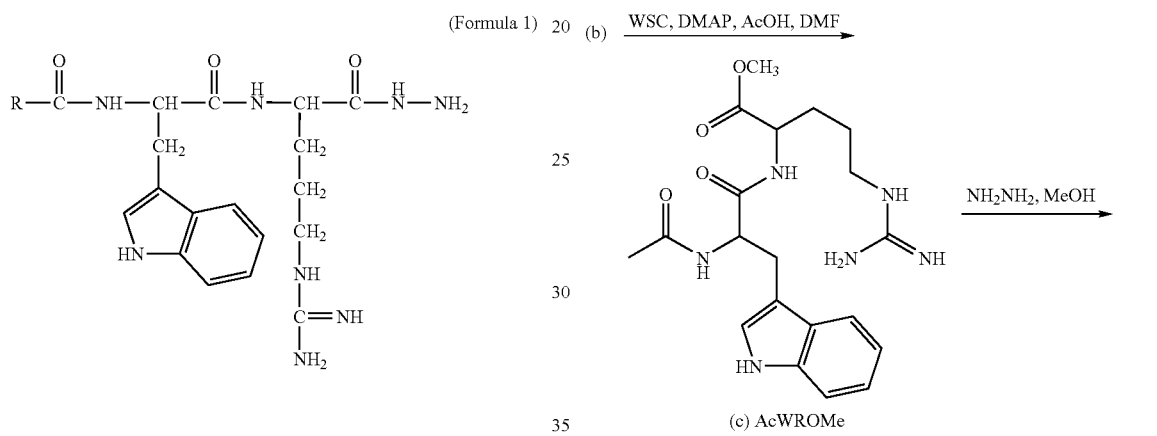

(Formula 1)

wherein, in the formula, R represents —$CH_3$ or —$CD_3$.

The compound of the formula (1) can be produced in accordance with the following Scheme 1, (Scheme 1)

[Chemical Formula 28]

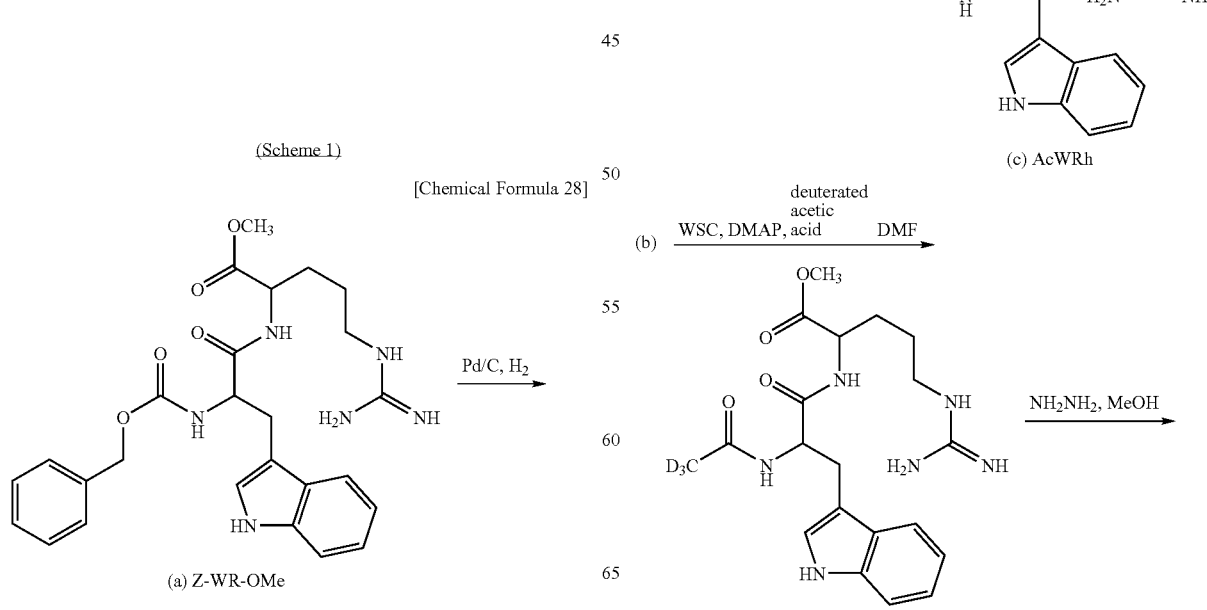

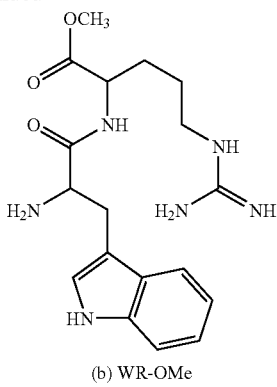

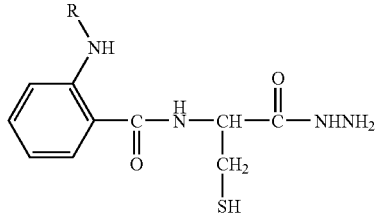

(e) d-AcWRh

In Scheme 1, the compound (b) can be obtained by subjecting the compound (a) in which the amino group of a tryptophan moiety is protected with the phenyl group or the like to deprotection by hydrogenation in the presence of Pd/C. Herein, the tryptophan moiety can also be substituted by phenylalanine, tyrosine, cysteine or the like.

Subsequently, the amino group in a tryptophan side of the compound (b) is acted on acetic acid (AcOH) in the presence of water-soluble carbodiimide (WSC) and dimethylaminopyridine (DMAP), in a solvent of dimethylformamide (DMF) for acetylation, whereby the compound (c) is obtained.

Furthermore, hydrazine is acted on the compound (c) in a solvent of methanol (MeOH) and a methoxy group of the C terminal end in an arginine side is substituted with a hydrazide group, whereby the compound (d) is obtained as a desired compound of the formula (1).

When a deuterium (D) is introduced into the compound (d), in Scheme 1, the compound (b) is acetylated in the presence of water-soluble carbodiimide (WSC) and dimethylaminopyridine (DMAP), in a solvent of dimethylformamide (DMF) using deuterated acetic acid (CD3COOH) to obtain a compound in which the amino group in a tryptophan side is acetylated using a deuterated acetyl group. Furthermore, hydrazine is acted on the compound in a solvent of methanol (MeOH) and a methoxy group of the C terminal end in an arginine side is substituted with a hydrazide group, whereby the compound (e) is obtained as a desired compound of the formula (1).

Meanwhile, as other example of the substance A, a compound having a structure of the following formula (2) can be cited,

[Chemical Formula 29]

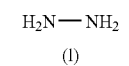

(Formula 2)

wherein, in the formula, R represents any of H, —COCH$_3$ or —COCD$_3$.

The compound of the formula (2) can be produced in accordance with the following Scheme 2,

[Chemical Formula 30]

(Scheme 2)

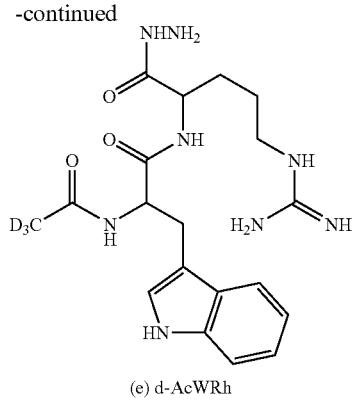

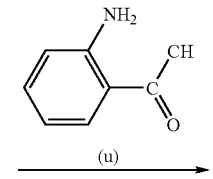

$\xrightarrow{(u)}$

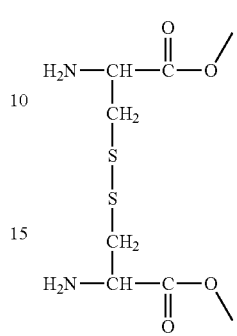

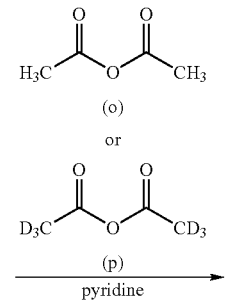

$\xrightarrow[\text{pyridine}]{(p)}$ (v)

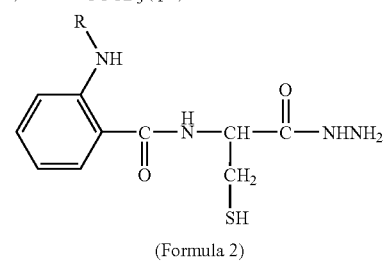

(q)

R = —COCH$_3$ (q-1) or —COCD$_3$ (q-2)

$\xrightarrow[(l)]{H_2N-NH_2}$ (Formula 2)

R = —COCH$_3$ (s-1) or —COCD$_3$ (s-2)

In Scheme 2, firstly, 2-aminobenzoic acid (compound (u)) is acted on a cysteine dimer (compound (t)), whereby the compound (v) is obtained.

Acetic anhydride is acted on this compound (v) for acetylating the amino group of the 2-aminobenzoyl group, whereby the compound (q) is obtained. At this time, a protinated compound (q-1) is obtained by using the compound (O) that is acetic anhydride. On the other hand, a deuterated compound (q-2) is obtained by using the compound (p) that is deuterated acetic anhydride.

Subsequently, the compound (q-1) or (q-2) is reacted with hydrazine, whereby the compound (r) is obtained. Incidentally, when R in the compound (r) is an acetyl group (—COCH3), a hydride (r-1) is obtained. When R is a deuterated acetyl group (—COCD3), a deuteride (r-2) is obtained.

Furthermore, there is obtained a compound containing a hydrazide group of the formula (2) having a 2-aminobenzoyl group in which the amino group is acetylated and cysteine by reducing the compound (r) by use of a reducing agent such as DTT or the like for cutting off the disulfide bond. Incidentally, when R in the compound (r) is an acetyl group (—COCH3), a hydride (s-1) is obtained. When R is a deuterated acetyl group (—COCD3), a deuteride (s-2) is obtained.

As described above, by introducing an arginine residue, a tryptophan residue, a phenylalanine residue, a tyrosine residue, a cysteine residue and a derivative thereof into the substance A, functions such as high sensitivity of mass spectrometry, fluorescence.UV labeling or the like can be provided to the captured sugar chain.

Further, as illustrated in the formula (2), chromophore or fluorophore of the 2-aminobenzoyl group or the like may be contained in a molecule. Examples of such a group include aromatic residues having typical examples of a benzyl group, a naphthyl group, an anthracenyl group, a pyridyl group and the like in addition to the 2-aminobenzoyl group; and substituents containing a Dansyl group or a Fmoc group. Such a substituent is a labeled compound for providing fluorescence, and generally used for HPLC analysis of the sugar chain. Accordingly, the sugar chain and/or the sugar derivative captured by using a substance A into which this substituent is introduced can be a labeled sample. By using this labeled sample, the sugar chain and/or the sugar derivative captured by using the substance A is enabled to be analyzed with high resolution and high sensitivity by HPLC employing a reverse phase column.

Furthermore, as explained in the formulae (1) and (2), a deuterated substituent, for example, a deuterated acetyl group or the like may be contained. A sample containing such a deuterated functional group is enabled to perform qualitative and quantitative analysis by enhancing the detection sensitivity by mass spectrometry.

For example, a deuterated sample by using the substance A of the formula (1) or (2) and a protinated sample are used in combination, whereby qualitative and quantitative analysis of the sugar chain contained, for example, in a sample containing an unknown sugar chain (for example, those obtained by treating serum) can be performed by mass spectrometry.

Accordingly, for example, when a sample with the composition and the concentration already known from the past is deuterium-labeled, an unknown sample is protium-labeled, and both samples are mixed for carrying out mass spectrometry, it is observed that each peak of the deuterated sample is shifted towards the high molecular weight as much as the number of introduced deuteriums rather than each peak corresponding to the protinated sample. Then, the position (m/z value) and intensity of each peak are analyzed so that the kind of the sugar chain illustrated by each peak of the unknown sample and the concentration in the sample are found. Such analysis can also be performed by making a known sample to a protium and an unknown sample to a deuterium.

Furthermore, in this analysis, a sample extracted from a healthy human is made to a deuterium, and a sample extracted from a disease patient is made to a protium, or a sample of a healthy human is made to a protium and a sample of a disease patient is made to a deuterium, whereby the difference in the kind and amount of the sugar chain contained in both samples can be analyzed. Accordingly, such an analytical sample can be suitably used for purposes of the pathological diagnosis on the basis of a biological reaction participating in the sugar metabolism, medical treatment by regulating such a biological reaction, and the like.

Regarding the substance A, the compound having a structure of the formulae (1) and (2) will be described below, but the substance A may be a substance selected from the following or a salt thereof, (substance A): 5-Dimethylaminonaphthalene-1-sulfonyl hydrazine (Dansylhydrazine); 2-hydrazinopyridine; 9-fluorenylmethyl carbazate (Fmoc hydrazine); benzylhydrazine; 4,4-difluoro-5,7-dimethyl-4-bora-3a,4a-diaza-s-indacene-3-propionic acid, hydrazide, 2-(6,8-difluoro-7-hydroxy-4-methylcoumarin)acetohydrazide; 7-diethylaminocoumarin-3-carboxylic acid, hydrazide (DCCH); phenylhydrazine; 1-Naphthaleneacethydrazide; 2-hydrazinobenzoic acid; biotin hydrazide; and phenylacetic hydrazide.

Further, from the viewpoint that the captured sugar chain is detected with high accuracy and high sensitivity, a moiety containing chromophore or fluorophore may be introduced or a deuterium may be introduced into these compounds.

Herein, the sugar chain capture reaction, that is, a reaction of the substance A with the sugar chain and/or the sugar derivative, is carried out by introducing the substance A into a sample containing the sugar chain and/or the sugar derivative. The reaction is carried out in the reaction system under conditions of pH of from 4 to 8, and the reaction temperature of from 4 to 90 degree centigrade, preferably from 25 to 90 degree centigrade and more preferably from 40 to 90 degree centigrade for 10 minutes to 24 hours, preferably 10 minutes to 8 hours and more preferably 10 minutes to 2 hours.

Furthermore, when a solid phase carrier is used, the substance A is represented by the following formula (3),

[Chemical Formula 31]

$$(\text{Carrier})\text{-R}—\text{NHNH}_2 \qquad \text{(Formula 3)}$$

wherein, in the formula, the carrier represents a polymer matrix; and R represents a hydrocarbon chain having 1 to 20 carbon atoms which may be interrupted with —O—, —S—, —NH—, —CO— or —CONH—.

In the formula (3), the carrier is a polymer matrix composed of an inorganic substance or an organic polymer substance, and is used in the form of a particle, or a solid phase substrate, or a substance directly bonded to a surface of the solid phase substrate.

Herein, as the inorganic substance which can be used as a carrier, a substance in the form of a particle can be used, and examples thereof include silica particles, alumina particles, glass particles, metal particles and the like.

Furthermore, examples of the organic polymer substance include polysaccharide gels having typical examples of agarose and sepharose, polymers of a vinyl compound in the form of a particle, and substances immobilized onto a surface of the solid phase substrate. Further, the surface of the solid phase substrate may be formed by using these substances.

Meanwhile, the polymer particle is preferably in the shape of a sphere, and is a polymer particle having its average particle diameter of equal to or more than 0.1 and equal to or less than 500 μm. The particle of the carrier having a particle diameter in such a range is easily subjected to recovery by centrifugation, filter or the like, and the reaction efficiency with the sugar chain is also considered to be high because the particle has a sufficient surface area. When the particle diameter is vastly greater than the above range, the reaction efficiency with the sugar chain is lowered in some cases since the surface area becomes small. Furthermore, when the particle diameter is vastly smaller than the above range, it is particularly difficult to recover the particle by the filter in some cases. Further, when the particle is filled in a column and the particle diameter is too small, the pressure loss at the time of passing the fluid is high in some cases.

Furthermore, examples of the solid phase substrate include a microplate and a flat substrate. In this way, an analytical sample can be prepared by applying the substance A to a substrate for a sugar chain microarray.

R represents a hydrocarbon chain having 1 to 20 carbon atoms which may be interrupted with —O—, —S—, —NH—, —CO— or —CONH—. For example, the following can be cited. In the following formula, a, b and d represent an integer of 1 to 5, while c represents an integer of 1 to 10,

[Chemical Formula 32]

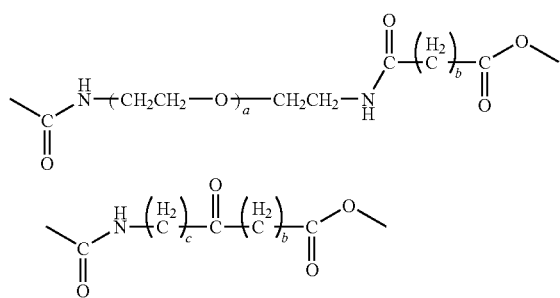

Herein, the sugar chain capture reaction may be carried out by filling the aforementioned substance A in the form of a particle in a column or the like and passing through the sample containing the sugar chain and/or the sugar derivative (continuous), or may be carried out by putting this particle into the sample and stirring (batch). Furthermore, the reaction may be carried out by continuously putting the sample into a reaction vessel filled with particles in advance and stirring (semi-batch).

Furthermore, the substance A represented by the above formula (3) can be obtained by polymerizing a raw material containing a carboxylic acid ester monomer having a polymerizable group in the presence of a crosslinking agent for obtaining a polymer particle containing carboxylic acid ester, and then treating the polymer particle containing carboxylic acid ester with a hydrazine solution of a concentration of not less than 10 volume percentage. Accordingly, from another viewpoint, the present invention provides a method for preparing such a substance A represented by the formula (3).

Herein, examples of the carboxylic acid ester monomer include N-hydroxysuccinimide esters of carboxylic acids and carboxylic acid methyl esters.

Meanwhile, as the crosslinking agent, a polyfunctional compound, a compound subjected to copolymerization with a carboxylic acid ester monomer, can be suitably used.

Examples thereof include (1) di or tri(meth)acrylic esters of polyols, for example, those ones in which the polyol is ethylene glycol, propylene glycol, trimethylol propane, glycerin, polyoxyethylene glycol, polyoxypropylene glycol, polyglycerin or the like, (2) in the above (1), unsaturated acid esters of polyols in which the unsaturated acid is other than (meth)acrylic acid, for example, maleic acid, fumaric acid or the like, (3) bisacrylamides, for example, N,N'-methylene bisacrylamide or the like, (4) di- or tri(meth)acrylic esters obtainable by reacting polyepoxides with (meth)acrylic acid, (5) di(meth)acrylic carbamyl esters obtainable by reacting polyisocyanates with (meth)acrylic hydroxyesters, for example, those ones in which the polyisocyanate is tolylene diisocyanate, hexamethylene diisocyanate or the like, and (6) polyvalent allyl compounds, for example, allylated starch, allylated cellulose, diallyl phthalate, tetraallyloxyethane, pentaerythritol triallyl ether, trimethylol propane triallyl ether, diethylene glycol diallyl ether, triallyl trimellitate or the like. Of these, ethylene glycol di(meth)acrylate, propylene glycol di(meth)acrylate, N,N'-methylene bis(meth)acrylamide and the like are preferable for use in the present invention.

Namely, the substance A represented by the formula (3) having the following structure can be used.

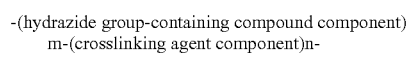

As the substance A having such a structure, those having a crosslinked polymer structure represented by the following formula (4) can be cited,

[Chemical Formula 33]

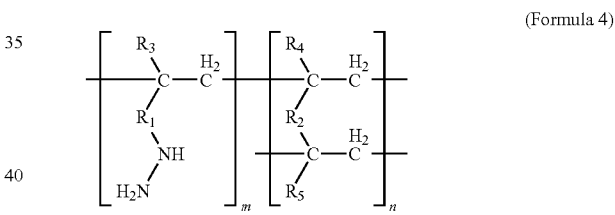

(Formula 4)

wherein, in the formula, $R_1$ and $R_2$ represent a hydrocarbon chain having 1 to 20 carbon atoms which may be interrupted with —O—, —S—, —NH—, —CO— or —CONH—; $R_3$, $R_4$ and $R_5$ represent H, $CH_3$ or a hydrocarbon chain having 2 to 5 carbon atoms; and m and n represent the number of monomer units.

$R_1$ represents a hydrocarbon chain having 1 to 20 carbon atoms which may be interrupted with —O—, —S—, —NH—, —CO— or —CONH—, and examples thereof include the same as those cited in the aforementioned R.

$R_2$ represents a hydrocarbon chain having 1 to 20 carbon atoms which may be interrupted with —O—, —S—, —NH—, —CO— or —CONH—, and examples thereof include the following. In the following formula, e and f represent an integer of 1 to 5, while g represents an integer of 1 to 10,

[Chemical Formula 34]

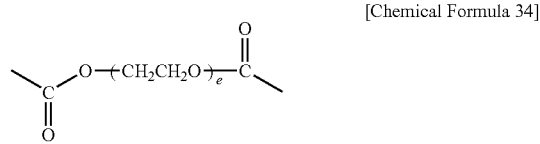

-continued

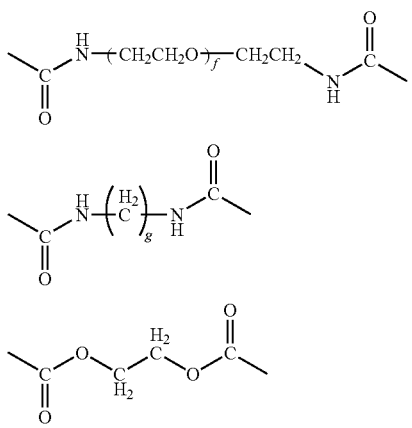

$R_3$, $R_4$ and $R_5$ may each be the same or different, and represent H, $CH_3$ or a hydrocarbon chain having 2 to 5 carbon atoms. Examples thereof include the following. In the following formula, h represents an integer of 1 to 4,

[Chemical Formula 35]

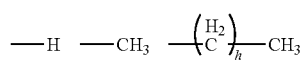

Herein, as the carboxylic acid ester monomer that is a precursor of the hydrazide group-containing compound component, carboxylic acid methyl ester monomer represented by the following formula (10) can be suitably used. Furthermore, as the crosslinking agent component, the aforementioned crosslinking agents can be used,

[Chemical Formula 36]

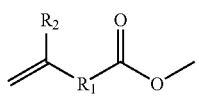

(Formula 10)

wherein, in the formula, $R_1$ represents a hydrocarbon chain having 1 to 20 carbon atoms which may be interrupted with —O—, —S—, —NH—, —CO— or —CONH—; and $R_2$ represents H, $CH_3$ or a hydrocarbon chain having 2 to 5 carbon atoms.

Concrete examples of $R_1$ and $R_2$ include the same as those cited in the aforementioned formula (4).

That is, the substance A represented by the formula (4) can be obtained by polymerizing a monomer having a structure of the formula (10) in the presence of a crosslinking agent for obtaining a polymer particle containing carboxylic acid ester, and then treating the polymer particle containing carboxylic acid ester with a hydrazine solution of a concentration of not less than 10 volume percentage.

From a further viewpoint, the present invention provides a preparation method for obtaining a substance A of the formula (4), as described above, using a monomer represented by the formula (10), a polymer obtained by polymerizing this monomer and this formula (10).

Furthermore, in this preparation method, when the carboxylic acid ester monomer is used as a starting material, this monomer is polymerized in the presence of a crosslinking agent to obtain a polymer particle, and then the polymer particle is treated with a hydrazine solution to obtain a substance A of the formula (4). However, for example, when the hydrazide group-containing monomer of the following formula (13) is used as a starting material, this monomer is polymerized in the presence of the aforementioned crosslinking agent and then subjected to deprotection, whereby a substance A of the formula (4) can also be obtained,

[Chemical Formula 37]

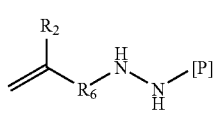

(Formula 13)

wherein, in the formula, $R_2$ represents H, $CH_3$ or a hydrocarbon chain having 2 to 5 carbon atoms; $R_6$ represents a hydrocarbon chain having 1 to 20 carbon atoms which may be interrupted with —O—, —S—, —NH—, —CO— or —CONH—; and [P] represents a protective group.

Herein, concrete examples of $R_2$ include the same as those cited in the aforementioned formula (4).

Furthermore, $R_6$ represents a hydrocarbon chain having 1 to 20 carbon atoms which may be interrupted with —O—, —S—, —NH—, —CO— or —CONH—, and examples thereof include the following. In the following formula, i and j represent an integer of 1 to 5,

[Chemical Formula 38]

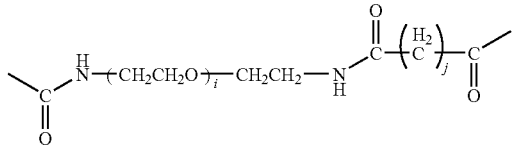

Furthermore, examples of the protective group [P] in the formula (13) include Boc, Fmoc, Tmoc and the like.

Meanwhile, as a method for deprotecting the protective group [P], a usual acid treatment can be cited.

From a further viewpoint, the present invention provides a preparation method for obtaining a substance A of the formula (4), as described above, using a monomer represented by the formula (13), a polymer obtained by polymerizing this monomer and, this formula (13).

Furthermore, of the formula (4), as the particularly suitable substance A, those having a crosslinked polymer structure represented by the following formula (5) can be cited,

[Chemical Formula 39]

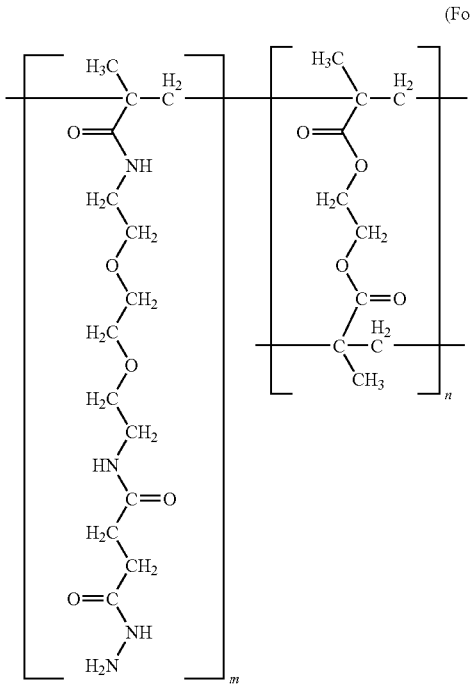

(Formula 5)

[Chemical Formula 40]

(Formula 11)

That is, the substance A represented by the formula (5) can be obtained by polymerizing a monomer having a structure of the formula (11) in the presence of a crosslinking agent for obtaining a polymer particle containing carboxylic acid ester, and then treating the polymer particle containing carboxylic acid ester with a hydrazine solution of a concentration of not less than 10 volume percentage.

From a further viewpoint, the present invention provides a preparation method for obtaining a substance A of the formula (5), as described above, using a monomer represented by the formula (11), a polymer obtained by polymerizing this monomer and, this formula (11).

Furthermore, in this preparation method, when the carboxylic acid ester monomer of the formula (11) is used as a starting material, this monomer is polymerized in the presence of a crosslinking agent to obtain a polymer particle, and then the polymer particle is treated with a hydrazine solution to obtain a substance A of the formula (5). However, for example, when the hydrazide group-containing monomer of the following formula (14) is used as a starting material, this monomer is polymerized in the presence of the aforementioned crosslinking agent and then subjected to deprotection, whereby a substance A of the formula (5) can also be obtained,

[Chemical Formula 41]

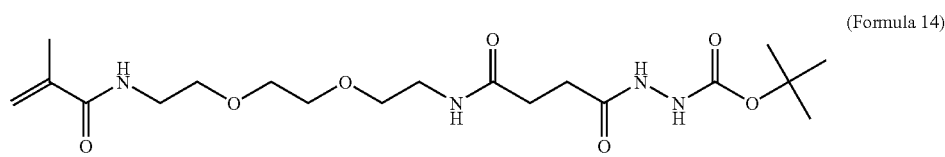

(Formula 14)

wherein, in the formula, m and n represent the number of monomer units.

Herein, as the carboxylic acid ester monomer that is a precursor of the hydrazide group-containing compound component, carboxylic acid methyl ester monomer represented by the following formula (11) can be suitably used. Furthermore, as the crosslinking agent component, ethylene glycol di(meth)acrylate can be used, Furthermore, as a method for deprotecting a t-butoxycarbonyl (Boc) group that is a protective group, a usual acid treatment can be cited.

From a further viewpoint, the present invention provides a preparation method for obtaining a substance A of the formula (5), as described above, using a monomer represented by the formula (14), a polymer obtained by polymerizing this monomer and, this formula (14).

Furthermore, the substance A represented by the formula (3), (4) or (5) is a polymer particle having a hydrazide group of a dry weight of not less than 100 nmol and preferably not less than 0.5 μmol per 1 mg. It is preferable that the substance is stable at the pH of 3 to 8, stable under pressure of at least not more than 1 MPa from the viewpoints that a shape of the particle is maintained and the content of the active hydrazide group is not substantially changed. Further, since the particle is copolymerized with a crosslinking agent, the solubility into a solvent is lowered, and the physical intensity is sufficiently obtained. Furthermore, there is no moiety to be cut off at the pH of 3 to 8.

From another viewpoint, the present invention provides a method for preparing a sample which involves the sugar chain capture step including binding a substance A to a sugar chain and/or a sugar derivative according to the aforementioned method for preparing a sample, and the sugar chain release step including the action of a substance B containing an aminooxy group or a hydrazide group on a complex of the substance A and the sugar chain and/or the sugar derivative captured in the sugar chain capture step, and binding the aforementioned sugar chain and/or sugar derivative while cut off from the aforementioned substance A to the substance B according to the hydrazone-oxime exchange reaction or the hydrazone-hydrazone exchange reaction occurred between the complex and the substance B.

In the sugar chain capture step of this method, as described above, the substance A and the sugar chain and/or the sugar derivative are bonded via hydrazone formation between the hydrazide group of the substance A and the reducing end of the sugar chain and/or the sugar derivative, thereby capturing the sugar chain and/or the sugar derivative using the substance A.

Subsequently, in the sugar chain release step, as shown in the following Reaction Formula (1), the hydrazone-oxime exchange reaction or the hydrazone-hydrazone exchange reaction is carried out,

[Chemical Formula 42]

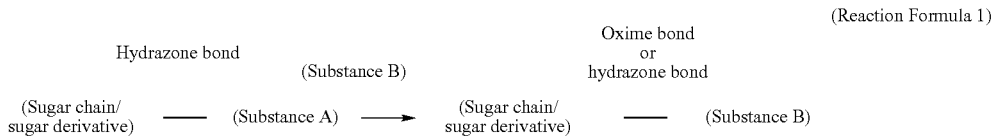

(Reaction Formula 1)

Herein, substances as described above can be used for the substance A.

Furthermore, the substance B may be in the form of either a low-molecular compound or a solid phase carrier.

When a low-molecular compound is used, it is preferable that the substance B contains a moiety consisting of at least one of an arginine residue, a tryptophan residue, a phenyla-lanine residue, a tyrosine residue, a cysteine residue and a derivative thereof from the aforementioned viewpoints, similar to the substance A.

That is, by an arginine residue or the like contained in the substance B, improvement in the detection sensitivity at the measurement of MALDI-TOF-MS, improvement in the reverse phase HPLC isolation, improvement in the fluorescence detection sensitivity and the like can be designed for the complex of the substance B and the sugar chain and/or the sugar derivative obtained through the sugar chain release step.

Examples of such a substance B include a low-molecular compound cited in the substance A and a compound having a structure represented by the following formula (7). Furthermore, in the formula (7), the tryptophan moiety can also be substituted by phenylalanine, tyrosine, cysteine or the like,

[Chemical Formula 43]

(Formula 7)

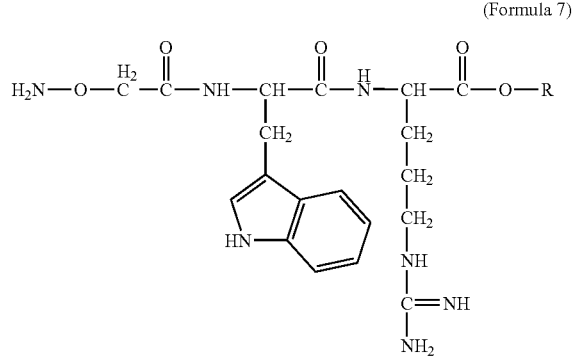

wherein, in the formula, R represents —$CH_3$ or —$CD_3$.

The compound of the formula (7) can be prepared in according with the following Scheme 3. Incidentally, R is $CH_3$, (Scheme 3)

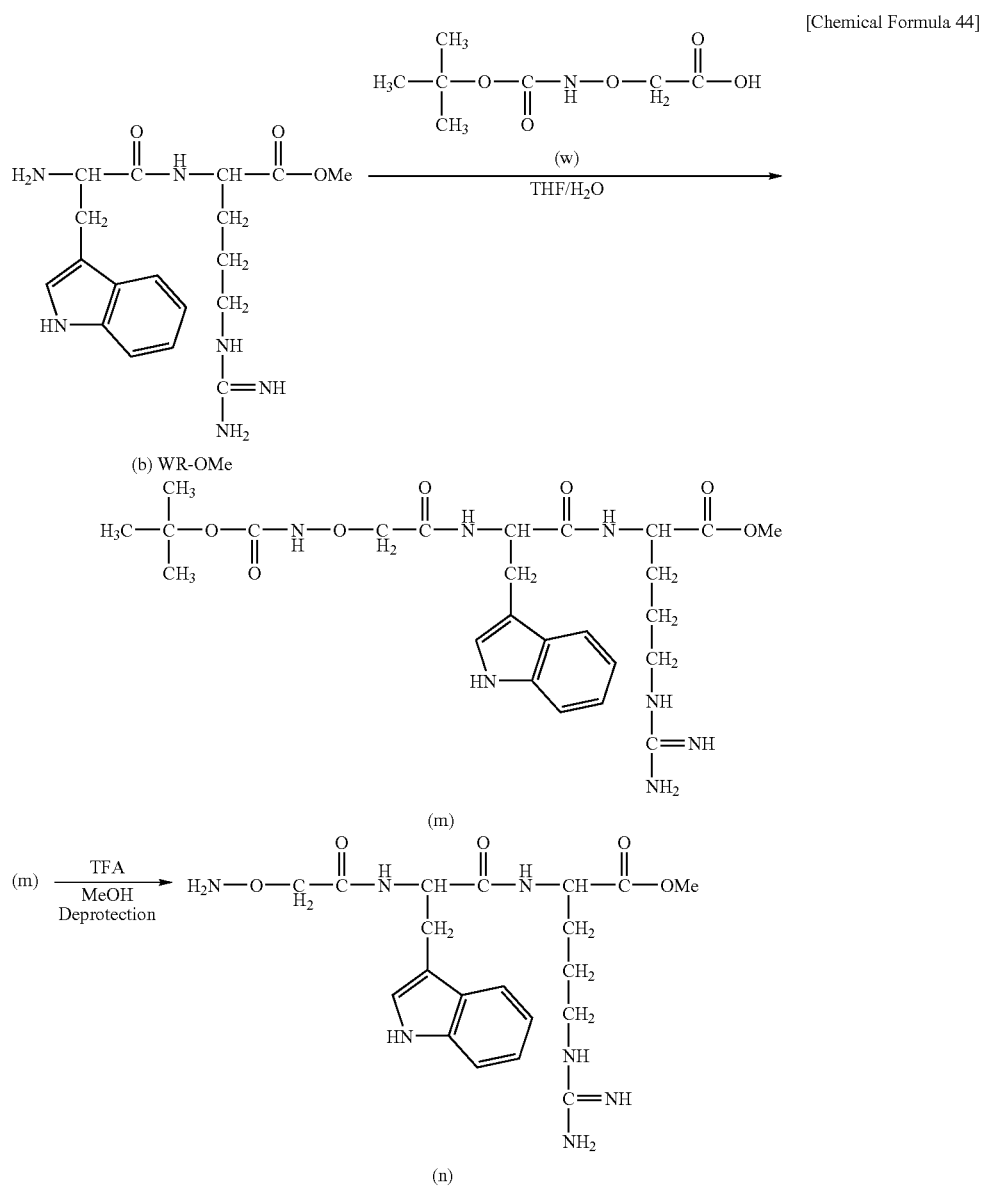

[Chemical Formula 44]

In Scheme 3, the compound (b) (WR-OMe) is obtained by subjecting the compound in which the amino group of the tryptophan moiety is protected by the phenyl group or the like to deprotection. Herein, the tryptophan moiety can also be substituted by phenylalanine, tyrosine or the like. Subsequently, the compound (m) is synthesized by the condensation reaction such as the mixed acid anhydride method or the like of the compound (b) and Boc-protected hydroxylamine (compound (w)). A protective group of this hydroxylamine is not restricted to Boc such as the compound (w), but may be Fmoc, Troc or the like. Subsequently, by subjecting the compound (m) to a deprotection procedure, the compound (n) is obtained as the compound of the formula (7), a desired product. As this deprotection procedure, for example, when a protective group is Boc, a procedure by trifluoroacetic acid (TFA) can be cited.

As described above, by introducing an arginine residue, a tryptophan residue, a phenylalanine residue, a tyrosine residue, a cysteine residue and a derivative thereof to the substance B, the captured sugar chain is enabled to be detected with high accuracy and high sensitivity.

Furthermore, as shown in the formula (7), chromophore or fluorophore of the 2-aminobenzoyl group or the like may be contained in a molecule. Examples of such a group include aromatic residues having typical examples of a benzyl group, a naphthyl group, an anthracenyl group, a pyridyl group and the like in addition to the 2-aminobenzoyl group; and substituents containing a Dansyl group or a Fmoc group. Such a substituent is a labeled compound for providing fluorescence, and is generally used for HPLC analysis of the sugar chain. Accordingly, the sugar chain and/or the sugar derivative captured by using the substance A into which this substituent is introduced can be made into a labeled sample. This labeled sample is used, whereby the sugar chain and/or the sugar derivative captured by using the substance A can be analyzed with high resolution and high sensitivity by HPLC employing a reverse phase column.

Furthermore, as described in the formula (7), a deuterated substituent, for example, a deuterated methoxy ester group or the like may be contained. Such a deuterated functional group contained therein enables to perform quantitative analysis using a difference in the mass numbers measured, for example, by mixing a standard substance with a sample at a state of the standard substance with heavy labeling and the sample with light labeling, in addition to an effect of enhancing the detection sensitivity by mass spectrometry.

According to this, a complex of the substance B and the sugar chain and/or the sugar derivative obtained through the sugar chain release step can also be suitably used for a complex of the aforementioned substance A and the sugar chain and/or the sugar derivative.

As for the substance B, a compound having a structure represented by the formula (7) is described, but the substance B may be a substance selected from the group consisting of the following substances containing a hydrazide group or the following substances containing an aminooxy group or a salt, (Substances containing a hydrazide group) 5-Dimethylaminonaphthalene-1-sulfonyl hydrazine (Dansylhydrazine); 2-hydrazinopyridine; 9-fluorenylmethyl carbazate (Fmoc hydrazine); benzylhydrazine; 4,4-difluoro-5,7-dimethyl-4-bora-3a,4a-diaza-s-indacene-3-propionic acid, hydrazide; 2-(6,8-difluoro-7-hydroxy-4-methylcoumarin)acetohydrazide; 7-diethylaminocoumarin-3-carboxylic acid, hydrazide (DCCH); phenylhydrazine; 1-Naphthaleneacethydrazide; 2-hydrazinobenzoic acid; and phenylacetic hydrazide, or (Substances containing an aminooxy group) O-benzylhydroxylamine; O-phenylhydroxylamine; O-(2,3,4,5,6-pentafluorobenzyl)hydroxylamine; O-(4-nitrobenzyl)hydroxylamine; 2-aminooxypyridine; 2-aminooxymethylpyridine; 4-[(aminooxyacetyl)amino]benzoic acid methyl ester; 4-[(aminooxyacetyl)amino]benzoic acid ethyl ester; and 4-[(aminooxyacetyl)amino]benzoic acid n-butyl ester.

Further, from the viewpoint that the captured sugar chain is detected with high accuracy and high sensitivity, a moiety containing chromophore or fluorophore may be introduced or a deuterium may be introduced into these compounds.

Herein, a reaction in the sugar chain release step is carried out by introducing the substance B into a sample containing the complex of the substance A and the sugar chain and/or the sugar derivative. The reaction is carried out by heating in the pH adjusted to 3 to 8 and preferably adjusted to 4 to 6 at a temperature of 4 to 90 degree centigrade and preferably 60 to 90 degree centigrade for 15 minutes to 16 hours, preferably 15 minutes to 5 hours and more preferably 30 minutes to 3 hours. As a solvent, preferably used is any of water, volatile organic solvents having typical examples of acetonitrile, methanol and the like, or a mixed solvent thereof. More preferably used is a mixed solvent of water and acetonitrile, and the most preferably used is a mixed solvent of water and acetonitrile (1:9) containing 2% acetic acid as a pH adjusting agent.

Meanwhile, when a solid phase carrier is used, substances cited in the aforementioned substance A, and substances containing an aminooxy group, for example, represented by the following formula (12) can be suitably used for the substance B,

[Chemical Formula 45]

$$(\text{Carrier})\text{-R}-\text{ONH}_2 \quad \text{(Formula 12)}$$

wherein, in the formula, the carrier represents a polymer matrix; and R represents a hydrocarbon chain having 1 to 20 carbon atoms which may be interrupted with —O—, —S—, —NH—, —CO— or —CONH—.

In the formula (12), the carrier is a polymer matrix composed of an inorganic substance or an organic polymer substance, similar to the carrier described in the formula (3), and is used in the form of a particle, or a solid phase substrate, or a substance directly bonded to a surface of the solid phase substrate. Furthermore, concrete examples of R include the same as those cited in the formula (3).

Herein, the exchange reaction of the sugar chain release step may be carried out by adding a solution of the substance B of a low-molecular compound to the substance A in the form of a particle capturing the sugar chain and/or the sugar derivative introduced into a vessel or the like. Furthermore, the exchange reaction may also be carried out by introducing the aforementioned substance B in the form of a particle into a vessel or the like, and adding a solution of the substance A of a low-molecular compound capturing the sugar chain and/or the sugar derivative. Or, the exchange reaction may be carried out such that the solution of the substance B of a low-molecular compound may be passing through the substance A in the form of a particle capturing the sugar chain and/or the sugar derivative filled in a column or the like. Further, the exchange reaction may also be carried out such that the aforementioned substance B in the form of a particle is filled in a column or the like through which the solution of the substance A of a low-molecular compound capturing the sugar chain and/or the sugar derivative is passed. Also, the exchange reaction may also be carried out such that the substance B of a low-molecular compound is introduced into the solution of the substance A of a low-molecular compound capturing the sugar chain and/or the sugar derivative.

In the complex of the substance B and the sugar chain and/or the sugar derivative obtained by this exchange reaction, the substance B and the sugar chain and/or the sugar derivative are bonded by a hydrazone bond when a substance having a hydrazide group is used as a substance B, and by an oxime bond when a substance having an aminooxy group is used as the substance B.

As the substance B represented by the formula (12), a polymer particle having a structure represented by the following formula (8) can be suitably used,

[Chemical Formula 46]

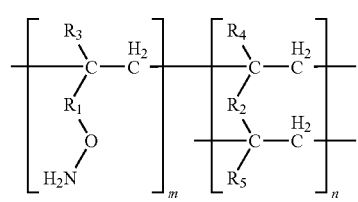

(Formula 8)

wherein, in the formula, $R_1$ and $R_2$ represent a hydrocarbon chain having 1 to 20 carbon atoms which may be interrupted with —O—, —S—, —NH—, —CO— or —CONH—; $R_3$, $R_4$ and $R_5$ represent H, $CH_3$ or a hydrocarbon chain having 2 to 5 carbon atoms; and m and n represent the number of monomer units. Furthermore, concrete examples of R1 to R5 include the same as those cited in the formula (4).

Furthermore, as such a polymer particle represented by the formula (8), a polymer particle having a structure represented by the following formula (9) can be suitably used,

[Chemical Formula 47]

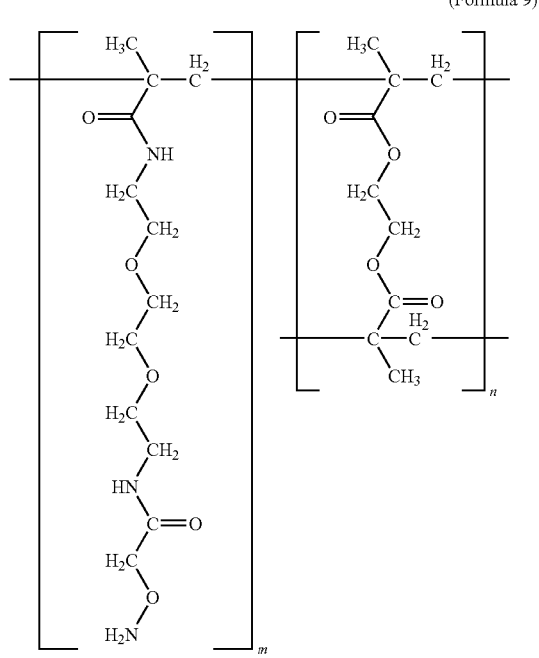

(Formula 9)

wherein, in the formula, m and n represent the number of monomer units.

Furthermore, it is preferable that the substance B represented by the formula (12), (8) or (9) is stable at the pH of 3 to 8 and stable under pressure of at least not more than 1 MPa from the viewpoints of the use of a sugar chain-capturing carrier and the use of a solid phase substrate.

Further, after the completion of the aforementioned sugar chain release step, the hydrazone-oxime exchange reaction or the hydrazone-hydrazone exchange reaction may be carried out at least one or more times. According to this, a labeled sample can be obtained by the action of the substance B composed of any optional labeled compound on the released sugar chain and/or the released sugar derivative so that the sample can be applied to the planned analysis method.

Herein, the method for obtaining a labeled sample by releasing the captured sugar chain using a sugar chain-capturing substance. However, according to the following method, a non-labeled sample can be obtained, and the present invention provides such a method for preparing a sample as well.

Such a method for preparing a sample is characterized in that the hydrazone bond is dissociated and the sugar chain and/or the sugar derivative is released by treating the substance A having a structure represented by the above formula (3), (4) or (5) under acidic conditions to which the sugar chain and/or the sugar derivative is bonded.

The treatment under acidic conditions at this time is carried out using a trifluoroacetic acid solution of 0.01 to 10 volume percentage and preferably a trifluoroacetic acid solution of 0.01 to 1 volume percentage at 25 to 80 degree centigrade for 5 to 60 minutes.

The thus-obtained analytical sample composed of the sugar chain sample is not labeled, and is useful for the application of those which may not be labeled.

In this way, it is possible to perform the separation and purification of the sugar chain and/or the sugar derivative for an analytical sample from a biological sample containing the sugar chain and/or the sugar derivative by a simple operation. From a further viewpoint, the present invention provides an analytical sample obtained by this method for preparing an analytical sample.

Furthermore, from another viewpoint, the present invention provides the use of the method for preparing a sample including the step of capturing the sugar chain by using the substance A. That is, the present invention provides a method of applying a solid phase carrier onto which a sugar chain and/or a sugar derivative obtained by subjecting a mixture or a specific fraction from the mixture to the isolation and purification is immobilized as a carrier for collecting a substance having a bonding property or affinity to the sugar chain and/or the sugar derivative.

In this application method, firstly, the sample containing the sugar chain and/or the sugar derivative may be used by subjecting a mixture or a specific fraction from the mixture to the isolation and purification. Furthermore, using a solid phase carrier as the substance A, the sample solution is passing through this solid phase carrier so that the sugar chain and/or the sugar derivative in this sample is bonded to the hydrazide group or the aminooxy group of the solid phase carrier and immobilized thereonto.

Subsequently, by the action of the sample (hereinafter referred to as a specimen sample) collected from a specimen for performing diagnosis or examination on this solid phase carrier, a substance having a bonding property or affinity to the sugar chain and/or the sugar derivative contained in this specimen sample, for example, a sugar binding protein such as lectin or the like is collected. In this way, the solid phase carrier onto which the sugar chain and/or the sugar derivative in the specimen sample is immobilized, and can be used as a carrier for collecting lectin or the like in the specimen sample.

Further, the collected substance is detected and quantitatively analyzed, whereby it is possible to perform the more advanced analysis of the relationship between the sugar chain and those of specimen cell differentiation, population growth, cell adhesion, immunity and a malignant change (cancer) of cells.

Furthermore, from another viewpoint, the present invention provides the use of the method for preparing a sample including the sugar chain capture step and the sugar chain release step.

From one viewpoint, the present invention provides a method for preparing a sugar chain microarray.

That is, in this method for preparing a sugar chain microarray, the sugar chain and/or the sugar derivative is immobilized onto a surface of the solid phase substrate composed of a solid phase carrier including a substance B having a structure represented by the following formula (3) or (12) according to the following steps (1) to (4),

[Chemical Formula 48]

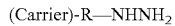 (Formula 3)

wherein, in the formula, the carrier represents a polymer matrix; and R represents a hydrocarbon chain having 1 to 20 carbon atoms which may be interrupted with —O—, —S—, —NH—, —CO— or —CONH—,

[Chemical Formula 49]

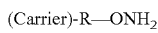
(Carrier)-R—ONH₂　　　　(Formula 12)

wherein, in the formula, the carrier represents a polymer matrix; and R represents a hydrocarbon chain having 1 to 20 carbon atoms which may be interrupted with —O—, —S—, —NH—, —CO— or —CONH—.

Incidentally, concrete examples of these substances include the same as those cited above.

(step 1) a step of purifying and/or isolating the sugar chain and/or the sugar derivative by a specific separation means by binding the sugar chain and/or the sugar derivative to a compound containing a soluble hydrazide group, (step 2) a step of dispensing drops of a solution of the compound obtained in the step (1) in a row onto the aforementioned solid phase substrate, (step 3) a step of proceeding a reaction of exchanging a sugar chain-substance A bond with a solid phase substrate-sugar chain bond by incubating the solid phase substrate after the completion of dispensing drops under prescribed conditions, and immobilizing the sugar chain and/or the sugar derivative onto the solid phase substrate, and (step 4) a step of washing and removing the unreacted substance on the solid phase substrate.

In the step (1), by reacting the aforementioned sugar chain and/or the sugar derivative with the substance A for capturing the sugar chain and/or the sugar derivative using the substance A, the sugar chain and/or the sugar derivative is purified and/or isolated by using a specific separation means, for example, a technique such as chromatography or the like. In the step (2), drops of the sugar chain and/or the sugar derivative obtained in the step (1) are dispersed onto the solid phase substrate in a row. In the step (3), the exchange reaction illustrated in the aforementioned Reaction Formula (1) is carried out by incubating the solid phase substrate under conditions of, for example, pH of 5, a temperature of 60 to 90 degree centigrade and a reaction time of 1 to 16 hours. As a result, the sugar chain and/or the sugar derivative is immobilized onto the solid phase substrate. In the step (4), the unreacted substance in the step (3) is washed and removed by a usual method using a buffer or the like.

From a further viewpoint, the present invention provides a sugar chain microarray obtained by such a method. This sugar chain microarray can be used as a carrier for collecting a substance which interacts, for example, with the sugar chain and/or the sugar derivative contained in the specimen sample. Accordingly, identification, quantitative analysis or the like of the collected substance can be performed.

From a further viewpoint, the present invention provides the use of the sugar chain microarray.

For example, a solution containing the specimen is brought into contact with a surface of this sugar chain microarray for incubating under prescribed conditions and washing, and then a sugar-binding substance collected at the sugar chain and/or the sugar derivative of a drop-dispersed region on the solid phase substrate is detected, whereby a system for searching the sugar-binding substance for specifically binding to or adsorbing the immobilized sugar chain and/or the immobilized sugar derivative is provided.

In this search system, in accordance with the aforementioned method, the solution containing a specimen (sample) is introduced into the solid phase substrate onto which the sugar chain and/or the sugar derivative is immobilized from an inlet tube or the like, and the specimen sample is brought into contact with the sugar chain and/or the sugar derivative.

Furthermore, in a state that the specimen sample is brought into contact with the sugar chain and/or the sugar derivative, the solid phase substrate is incubated. Incubation at this time is carried out under conditions of, for example, pH of 4 to 10, a temperature of 37 degree centigrade and a reaction time of 1 to 16 hours.

As a result of incubation, the sugar-binding substance collected at the sugar chain and/or the sugar derivative, for example, protein such as lectin or the like is detected. As the detection method and means at this time, when the sugar-binding substance can be directly fluorescent dyed, fluorescence is measured by using a fluorescent scanner after the completion of dyeing, whereby the substance is detected; and when a sugar-binding substance is already known and is bonded to a specific antibody, the antibody is bonded, whereby the substance is detected. Further, when a sugar-binding substance is protein, the method is not restricted thereto, and other general methods for detecting protein can be applied.

According to this system, the collected sugar-binding substance is detected, whereby the sugar-binding substance for specifically binding to or adsorbing the immobilized sugar chain and/or the immobilized sugar derivative can be searched. According to this, it is possible to perform the more advanced analysis of the relationship between the sugar chain and specimen cell differentiation, population growth, cell adhesion, immunity and a malignant change (cancer) in cells.

Further, there is provided a system for evaluating the recognition specificity of a binding protein, for example, as the use of the aforementioned sugar chain microarray, by bringing a solution containing a specimen into contact with a surface of the sugar chain microarray, collecting a sugar binding protein in the specimen at the sugar chain and/or the sugar derivative of a drop-dispersed region on the solid phase substrate, and quantitatively analyzing the collected amount by a prescribed means, for example, fluorescence, color development or the like.

As described above, the sugar binding protein in the specimen sample is collected at the sugar chain microarray composed of the solid phase substrate onto which the sugar chain and/or the sugar derivative is immobilized, and the collected amount is quantitatively analyzed.

According to this system, based on the result, the recognition specificity of the binding protein can be evaluated.

Furthermore, from another viewpoint, the present invention provides a method for preparing sugar chain affinity beads as the use of the method for preparing a sample including the sugar chain capture step and the sugar chain release step.

That is, the method for preparing sugar chain affinity beads includes immobilizing the sugar chain and/or the sugar derivative onto the surface of the polymer composed of the solid phase carrier consisting of the substance B having a structure represented by the following formula (3) or (12),

[Chemical Formula 50]

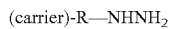
(carrier)-R—NHNH₂　　　　(Formula 3)

wherein, in the formula, the carrier represents a polymer matrix; and R represents a hydrocarbon chain having 1 to 20 carbon atoms which may be interrupted with —O—, —S—, —NH—, —CO— or —CONH—,

[Chemical Formula 51]

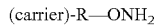
(carrier)-R—ONH₂　　　　(Formula 12)

wherein, in the formula, the carrier represents a polymer matrix; and R represents a hydrocarbon chain having 1 to 20 carbon atoms which may be interrupted with —O—, —S—, —NH—, —CO— or —CONH—.

Incidentally, concrete examples of these substances include the same as those described above.

Furthermore, in the method for preparing the sugar chain affinity beads, the sugar chain and/or the sugar derivative may be immobilized onto the surface of the polymer particle according to the following steps (1) to (3), (step 1) a step of purifying and/or isolating the sugar chain and/or the sugar derivative by a specific separation means by binding the sugar chain and/or the sugar derivative to a compound containing a soluble hydrazide group, (step 2) a step of immobilizing the sugar chain and/or the sugar derivative onto the polymer particle by bringing the compound obtained in the step (1) into contact with the polymer particle and incubating under prescribed conditions for exchanging a sugar chain-hydrazide group-containing compound bond with a sugar chain-polymer particle bond, and (step 3) a step of washing and removing the unreacted substance on the polymer particle.

In the step (1), by reacting the aforementioned sugar chain and/or the sugar derivative with the substance A for capturing the sugar chain and/or the sugar derivative using the substance A, the sugar chain and/or the sugar derivative is purified and/or isolated by using a specific separation means, for example, a technique such as chromatography or the like. Incidentally, concrete examples of the conditions of the sugar chain capture reaction at this time include conditions of pH of 4 to 7, a reaction temperature at 25 to 90 degree centigrade and a reaction time for 1 to 16 hours, specifically pH of 5, a reaction temperature at 80 degree centigrade and a reaction time for 1 hour.

In the step (2), the exchange reaction illustrated in the aforementioned Reaction Formula (1) is carried out by brining the sugar chain and/or the sugar derivative obtained in the step (1) into contact with the polymer particle and incubating the solid phase substrate under specific conditions of, for example, pH of 4 to 7, a temperature at 25 to 90 degree centigrade and a reaction time for 1 to 16 hours, specifically pH of 5, a temperature at 80 degree centigrade and a reaction time for 1 hour. As a result, the sugar chain and/or the sugar derivative is immobilized onto the polymer particle. In the step (3), the unreacted substance in the step (2) is washed and removed by a usual method using a buffer or the like.

Incidentally, the sugar chain and/or the sugar derivative is captured by using the substance A having a hydrazide group in advance and the exchange reaction is carried out by using the substance B, whereby sugar chain affinity beads are prepared. The procedure for preparing sugar chain affinity beads is not restricted thereto. The sample containing the sugar chain and/or the sugar derivative is directly brought into contact with the polymer particle prepared using the solid phase carrier consisting of the substance B, whereby the sugar chain affinity beads may be prepared.

From a further viewpoint, the present invention provides sugar chain affinity beads obtained in accordance with such a method. Further, the present invention provides a system for isolating the sugar-binding substance for the use of the sugar chain affinity beads.

That is, in the system for isolating the sugar-binding substance, a solution containing the specimen (sample) is brought into contact with the aforementioned sugar chain affinity beads for incubating under prescribed conditions and washing, and then the captured sugar-binding substance is isolated.

In this system, firstly, a solution containing the specimen sample is brought into contact with the sugar chain affinity beads for incubating in a buffer solution containing $Ca^{2+}$ and $Mg^{2+}$ under specific conditions of, for example, pH of 4 to 10, a temperature at 37 degree centigrade and a reaction time for 1 to 16 hours, whereby a sugar-binding substance is collected at the sugar chain and/or the sugar derivative which is immobilized onto a surface of the sugar chain affinity beads. Furthermore, the surface of the sugar chain affinity beads at which the sugar-binding substance is collected is washed by the usual washing procedure using a buffer or the like.

Furthermore, the collected sugar-binding substance is isolated from the sugar chain affinity beads. At this time, as a method for releasing the sugar-binding substance from the sugar chain affinity beads, there can be exemplified, for example, a method including adding an organic solvent such as methanol or the like and separating a sugar and a sugar-binding substance; a method including adding a solution of hapten sugar of a high concentration (0.1 to 1M) and separating a sugar-binding substance, i.e., transferring lectin to the added sugar of a high concentration; and the like.

As described above, the method for preparing a sample of the present invention can be applied to various purposes.

EXAMPLES

The present invention is now illustrated in detail below with reference to the following Experimental Examples. However, the present invention is not restricted to these Experimental Examples.

Experimental Example 1

(A) Preparation of Hydrazide Group-Containing Compound

Low-Molecular Hydrazide Compound

1. Commercial products were used for the following hydrazide compounds,

5-Dimethylaminonaphthalene-1-sulfonyl hydrazine (Dansylhydrazine); 2-hydrazinopyridine; 9-fluorenylmethyl carbazate (Fmoc hydrazine); benzylhydrazine; 4,4-difluoro-5,7-dimethyl-4-bora-3a,4a-diaza-s-indacene-3-propionic acid, hydrazide (BODIPY™ FL hydrazide); 2-(6,8-difluoro-7-hydroxy-4-methylcoumarin)acetohydrazide (Marina Blue™ hydrazide); 7-diethylaminocoumarin-3-carboxylic acid, hydrazide (DCCH); phenylhydrazine; 1-Naphthaleneacethydrazide; and 2-hydrazinobenzoic acid.

2. Synthesis of AcWRh (Substance A)

AcWRh was synthesized through the route illustrated in the aforementioned Scheme 1 (incidentally, Ac represents an acetyl group, W represents a tryptophan residue, R represents an arginine residue, and h represents a hydrazide group).

(1) Synthesis of WR-OMe (Compound (b))

Methanol (5 ml) was added to Z-WR-OMe (a) (10 mg, 20 mmol) and 10% Pd/C (10 mg), and the resulting mixture was stirred in a hydrogen gas atmosphere at room temperature for 2 hours. The reaction solution was filtered using an aqueous membrane filter to remove Pd/C and the filtrate was concentrated under a reduced pressure, whereby a desired compound (b) (WR-OMe) was obtained. By the analysis according to MALDI-TOF-MS, a desired product, the $[M+H]^+$ ion was observed at m/z: 376.

(2) Synthesis of AcWROMe (c)

WR-OMe (b) (53 mg, 0.14 mmol) was dissolved in 1 ml of DMF, and WSC (40 mg, 0.20 mmol), DMAP (5 mg, 0.041 mmol) and acetic acid (200 μl) were added thereto. The resulting mixture was stirred at room temperature for 3 hours. Furthermore, WSC (50 mg, 0.26 mmol) was added and stirred all night. The reaction solution was concentrated, and the obtained residue was purified by silica gel column chromatography (chloroform:methanol=1:1), whereby a desired AcWROMe was obtained.

1H NMR (500 MHz, CD3OD) δ7.70-7.00 (m, 5H, indole), 3.62 (s, 3H, OMe), 1.93 (s, 3H, Ac).

(3) Synthesis of AcWRh (d)

10 mg of AcWROMe was dissolved in 10% hydrazine/methanol (5 ml), and the resulting solution was reacted at room temperature for 12 hours and then concentrated, whereby AcWRh (d) was prepared. By the analysis according to MALDI-TOF MS, a desired product, the $[M+H]^+$ ion was observed at m/z: 416.89.

On the other hand, according to the above procedure, d-AcWRh (e) in which an acetyl group was substituted by a deuterium was prepared.

d-AcWROMe: 1H NMR (500 MHz, CD3OD) δ7.59-6.99 (m, 5H, indole), 3.62 (s, 3H, OMe), 1.93 (s, 3H, Ac), d-AcWRh: MALDI-TOF-MS [M+H]+ m/z: 419.94

Synthesis of Hydrazide Group-Containing Polymer Beads

1. Synthesis of Methyl Ester-Containing Monomer

A methyl ester-containing monomer was synthesized through the route illustrated in the following Scheme 4,

[Chemical Formula 52]

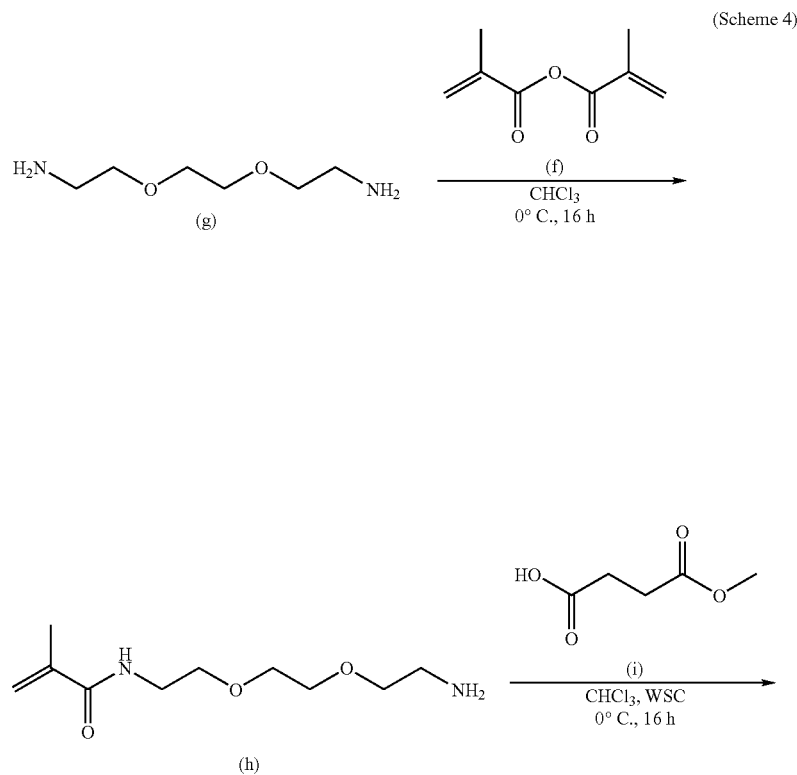

(1) Synthesis of Compound (H)

A solution prepared by dissolving methacrylic anhydride (MAH: 5 g, 0.03 mol) (f) in 100 ml of chloroform was put dropwise, on an ice bath, to a solution prepared by dissolving 25 g of (ethylenedioxy)bis(ethylamine) (EDBEA: 25 g, 0.17 mol) (g) in 100 ml of chloroform. The resulting material was filled with nitrogen and the content was stirred all night. The residue obtained by evaporating a solvent from the obtained reaction solution was applied to silica gel column chromatography (development solvent: mixed solvent of 90 volume % chloroform/10 volume % methanol) for taking out a prescribed fraction, and the solvent was evaporated from this fraction, whereby a compound (h) was obtained.

(2) Synthesis of Compound (j)

content was stirred all night. The residue obtained by evaporating a solvent from the obtained reaction solution was applied to silica gel column chromatography (development solvent: mixed solvent of 90 volume % chloroform/10 volume % methanol) for taking out a prescribed fraction, and the solvent was evaporated from this fraction, whereby a compound (j) was obtained.

Furthermore, the obtained substance was confirmed to be the compound (j) by NMR and a matrix-assisted laser-desorption ionized time-of-flight mass spectrometer (MALDI-TOF-MS).

2. Synthesis of Methyl Ester-Containing Polymer

A polymer particle containing methyl ester was synthesized through the route illustrated in the following Scheme 5,

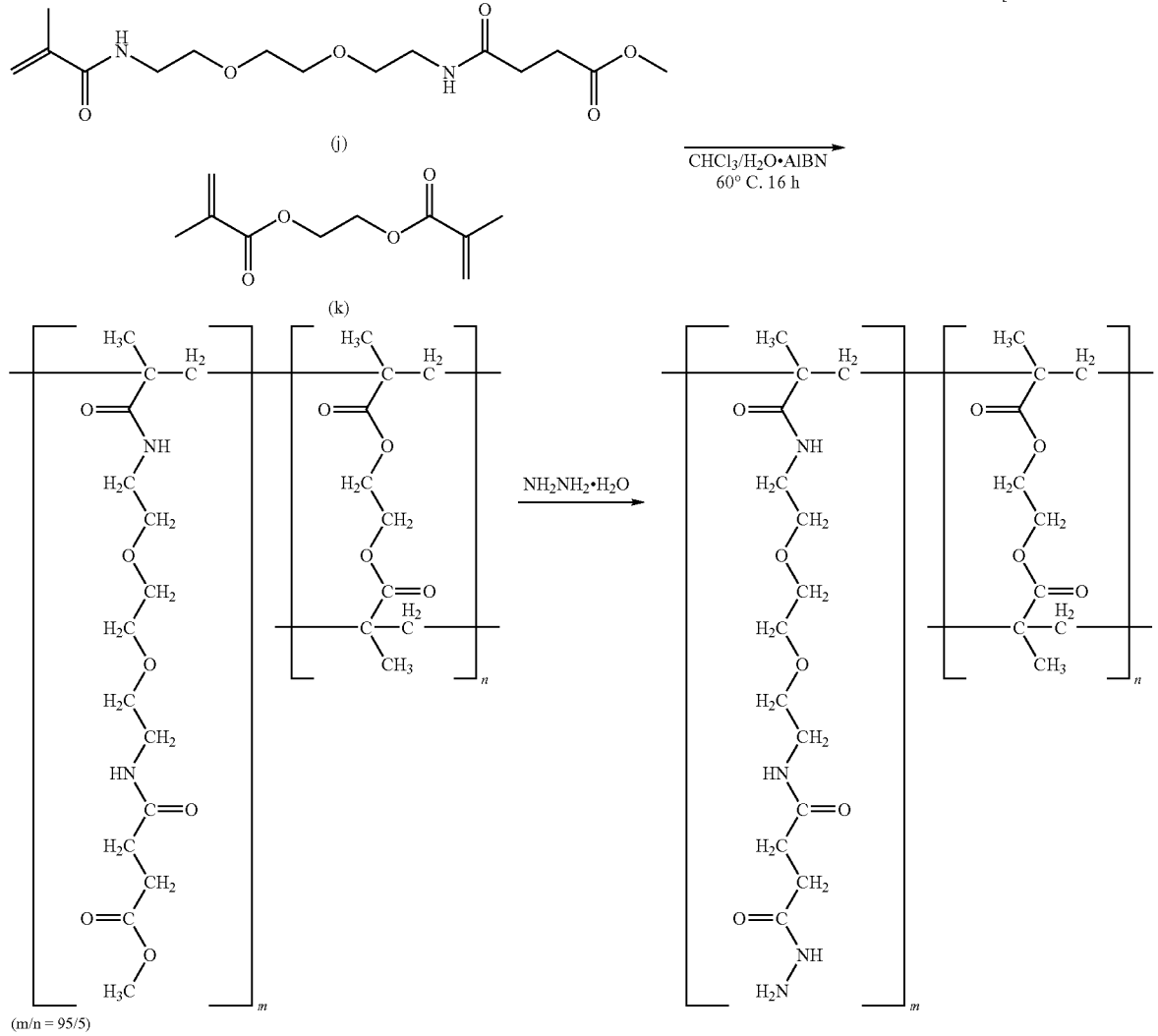

To a solution prepared by dissolving 5 g of the compound (h) (0.023 mol) in 100 ml of chloroform were added 1.5 equivalents of monomethyl succinate (i) and 1.5 equivalents of a water-soluble carbodiimide compound (WSC), i.e., 1-ethyl-3-(3-dimethylaminopropyl)carbodiimide. The reaction vessel was tightly sealed and filled with nitrogen, and the Into a three-necked flask was introduced 25 ml of a 5% aqueous solution of polyvinyl alcohol (PVA) and purged with nitrogen. A mixture composed of 1 g (2.6 mmol) of the compound (j), ethylene glycol dimethacrylate (k) (EGDMA: 5 mol % with respect to (j)) and 1 ml of chloroform was introduced into said three-necked flask, and the reaction solution was stirred while the temperature was maintained at 60 degree centigrade to disperse the compound (j) and EGDMA, which were monomers contained in the mixture, in the aqueous PVA solution. Subsequently, to start polymerization, azobisisobutyronitrile (AIBN) was added as a polymerization initiator in an amount of 3 weight % with respect to the monomer. The reaction was carried out at 60 degree centigrade for 16 hours, and then the resultant polymer particles were collected by centrifugation and washed with methanol and water.

3. Introduction of Hydrazide Group 400 mg of a polymer particle was taken in a vessel, 4 ml of hydrazine monohydrate was added, and the resulting mixture was stirred and allowed to stand at room temperature for 2 hours. After the reaction, hydrazine monohydrate was removed, and the resulting reactant was washed with methanol, and then rinsed with 1M hydrochloric acid. Thereafter, the resulting reactant was further washed with pure water.

4. Quantitative Analysis of Amount of Functional Group 1 mg of a polymer particle was taken in a vessel. 1 µmol of N-acetyl-D-lactosamine (LacNAc) was added thereto, and 180 µl of acetonitrile containing 2% acetic acid was further added. The resulting material was heated at 80 degree centigrade for 45 minutes, whereby LacNAc and a hydrazide group on beads were reacted. Beads were rinsed with pure water so that the unreacted sugar chain was recovered and quantitatively analyzed by the measurement of MALDI-TOF-MS (internal standard method) to obtain the bonding amount of LacNAc with beads. It was found that 0.86 µmol (860 nmol) of LacNAc was bonded per 1 mg of beads.

Commercial Hydrazide Group-Containing Beads

Affi-Gel Hz manufactured by Bio-Rad Co., Ltd. was used as it was.

1. Quantitative Analysis of Amount of Functional Group

50 µl (16.5 mg as a dry weight of beads) of a dispersion of Affi-Gel Hz was taken in a vessel. 1 µmol of LacNAc was added thereto, and 180 µl of acetonitrile containing 2% acetic acid was further added. The resulting material was heated at 80 degree centigrade for 45 minutes, whereby LacNAc and a hydrazide group on beads were reacted. Beads were rinsed with pure water so that the unreacted sugar chain was recovered and quantitatively analyzed by the measurement of MALDI-TOF-MS (internal standard method) to obtain the bonding amount of LacNAc with beads. It was found that about 8 nmol of LacNAc was bonded per 1 mg of beads (dry weight).

(B) Synthesis of Aminooxy Group-Containing Compound

Synthesis of Aminooxy Group-Containing Low-Molecular Compound aoWR aoWR (compound (n)) was synthesized according to the aforementioned. Scheme 3 (ao represents an aminooxy group).

(1) Synthesis of Boc-NHOCH2CO—W—R-OMe (Compound (m))

A THF (6 ml) solution of Boc aminooxyacetic acid (1) (2.5 mmol) was cooled down to −20 degree centigrade. Next, N-methylmorpholine (3.0 mmol) and isobutyl formate (3.0 mmol) were added thereto, and the resulting mixture was stirred for 15 minutes, whereby a mixed acid anhydride was prepared. The reaction solution was at a temperature of 0 degree centigrade, the compound (b) (WR-OMe (3.0 mmol)) was dissolved in water (3 ml), and sodium hydrogen carbonate (3.0 mmol) was added to prepare a WR-OMe solution. The WR-OMe solution was mixed with another reaction solution and the resulting mixture was stirred for 1 hour. The reaction solution was concentrated under a reduced pressure, and the obtained residue was purified by silica gel column chromatography, whereby a desired compound (m) (Boc-NHOCH2CO—W—R-OMe) was obtained. By the analysis according to MALDI-TOF-MS, a desired product, the [M+H]+ ion was observed at m/z: 547.

(2) Synthesis of NH2OCH2CO—W—R-OMe (Compound (n))

To the compound (m) was added trifluoroacetic acid (TFA) (2 ml), and the resulting mixture was stirred at −20 degree centigrade for 2 hours. The reaction solution was concentrated under a reduced pressure, toluene was added and the reaction solution was repeatedly azeotroped to remove TFA, whereby a desired compound (n) was obtained. By the analysis according to MALDI-TOF-MS, a desired product, the [M+H]+ ion was observed at m/z: 448.

On the other hand, in accordance with the above procedure, aoWR (H) in which hydrogen of a methyl group was protium and aoWR (D) in which hydrogen was deuterium were prepared.

Synthesis of Aminooxy Group-Containing Polymer Beads

A polymer particle containing an aminooxy group was prepared according to the method as described in Patent Document: International Publication Pamphlet No. 2005/097844.

Experimental Example 2

Preparation of Sugar Chain Sample (1) Preparation of Glycoprotein Sugar Chain

Fetuin was used as glycoprotein or ribonuclease B was used as a sample. 10 mg of glycoprotein was taken in a vessel and dissolved in a 50 mM ammonium bicarbonate solution. A small amount of a surface active agent was added thereto and the reaction solution was incubated at 60 degree centigrade for 30 minutes, and then 10 units of N-glycosidase F (a product of Roche) were added, and the resulting solution was incubated at 37 degree centigrade for 16 hours, whereby a sugar chain was released.

(2) Preparation of Glycoprotein Sugar Chain Contained in Serum 5 mL of normal serum was taken in a vessel and dissolved in a 50 mM ammonium bicarbonate solution. A small amount of a surface active agent was added thereto and the reaction solution was incubated at 60 degree centigrade for 30 minutes, and then 5 units of N-glycosidase F (a product of Roche) were added, and the resulting solution was incubated at 37 degree centigrade for 16 hours, whereby a sugar chain was released.

Experimental Example 3

Reaction of Low-Molecular Hydrazide Compound with Sugar Chain (1) Reaction of Commercial Hydrazide Compound with Sugar Chain The hydrazide compound of Experimental Example 1 (A) with a concentration of 10 mM was dissolved in methanol or acetonitrile to obtain a hydrazide compound solution. To the fetuin sugar chain solution of Experimental Example 2(1) (corresponding to 500 µmol) were added 1 µl of a hydrazide compound solution and further 100 µl of acetonitrile. The reaction solution was heated at 80 degree centigrade for 45 minutes, whereby the sugar chain and the hydrazide compound were reacted. The product after the completion of the reaction was measured by MALDI-TOF-MS.

FIG. 1 illustrates a MALDI-TOF-MS chart when 2-hydrazinopyridine was typically used, whereas a peak was observed at the position indicating the molecular weight of the sugar chain (in the figure, a structure represented in a schematic view) and 2-hydrazinopyridine bonded to each other. The same results were also obtained when other compounds were used.

(2) Reaction of AcWRh with Sugar Chain

AcWRh of Experimental Example 1(A) was dissolved to the concentration of 10 mM in methanol or acetonitrile to obtain a hydrazide compound solution. The serum sugar chain solution (corresponding to 5 µl of serum) of Experimental Example 2(2) was taken in a vessel. 1 µl of the hydrazide compound solution was added thereto and 100 µl of acetonitrile was further added. The resulting material was heated at 80 degree centigrade for 45 minutes, whereby the sugar chain and the hydrazide compound (AcWRh) were reacted. The product after the completion of the reaction was measured by MALDI-TOF-MS.

Figure 2:
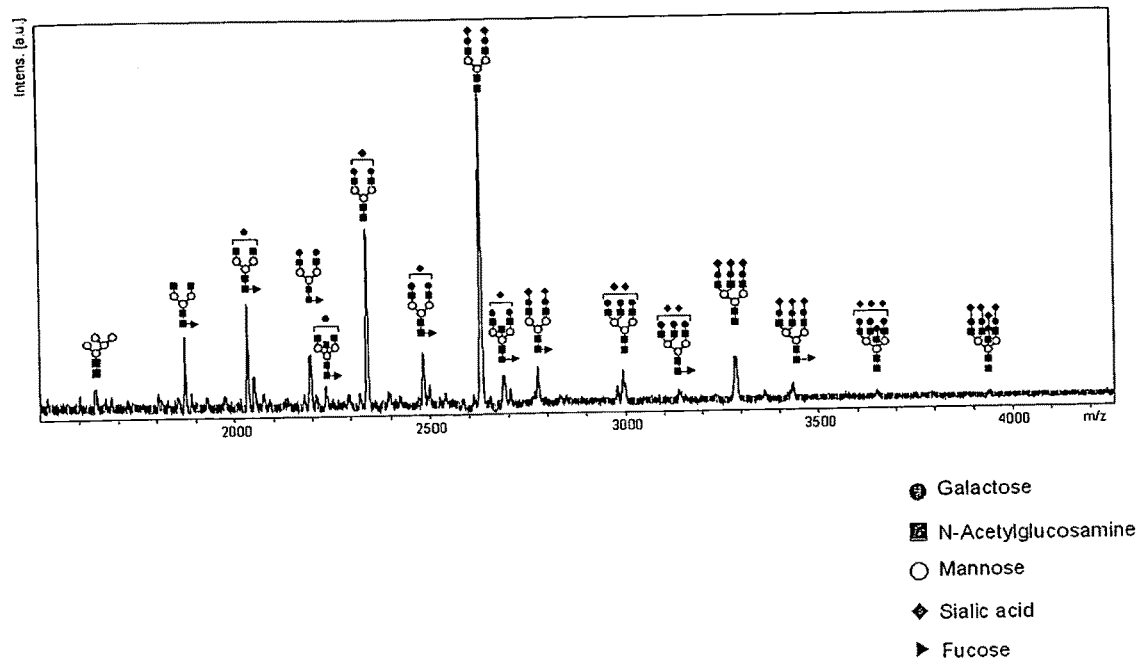
FIG. 2 illustrates a MALDI-TOF-MS chart of the reactant of a sugar chain and a substance A of the Example. The horizontal axis represents the molecular weight (m/z), while the vertical axis represents the intensity. Structures of the sugar chain expected at each main peak are schematically represented by ●: galactose, ■: N-acetylglucosamine, ○: mannose, ◆: sialic acid and triangle figure: fucose.

FIG. 2 illustrates a MALDI-TOF-MS chart, whereas a peak was observed at the position indicating the molecular weight of the sugar chain (in the figure, a structure represented in a schematic view) and AcWRh bonded to each other.

Experimental Example 4

Reaction of Hydrazide Group-Containing Polymer Beads with Sugar Chain 2.5 mg of the polymer beads containing a hydrazide group of Experimental Example 1 (A) was measured in a vessel. The serum sugar chain solution (corresponding to 5 µl of serum) of Experimental Example 2(2) was added, and 180 µl of acetonitrile containing 2% acetic acid was further added. The resulting material was heated at 80 degree centigrade for 45 minutes, whereby the sugar chain and a hydrazide group on beads were reacted. Beads were rinsed with a small amount of pure water so that the unreacted sugar chain was recovered and quantitatively analyzed by the measurement of MALDI-TOF-MS (internal standard method). As a result, it was found that 80 to 90% sugar chain was bonded to beads. Thereafter, beads were washed with a 0.5% aqueous solution of sodium dodecyl sulfate (SDS), 50% methanol, an aqueous solution of 4M guanidine and pure water, and supplied to the experiment of re-releasing of the sugar chain to be described below.

Experimental Example 5

Preparation of Labeled Sugar Chain (1) Bonding of AcWRh (d), AcWRh (e) and Sugar Chain To an aqueous chitotriose solution was added 10 equivalents of AcWRh (d) or d-AcWRh (e) of Experimental Example 1(A), and the pH was adjusted to 5 with acetic acid. The reaction solution was heated at 90 degree centigrade for 1 hour, whereby a labeled chitotriose-AcWRh (d) and a labeled chitotriose-d-AcWRh (e) were obtained.

(2) Bonding of aoWR (H), aoWR (D) and Sugar Chain

To an aqueous chitotriose solution was added 10 equivalents of aoWR (H) or aoWR (D) of Experimental Example 1(B), and the pH was adjusted to 5 with acetic acid. The reaction solution was heated at 90 degree centigrade for 1 hour, whereby a labeled chitotriose-aoWR was obtained.

Experimental Example 6

Liquid Phase Exchange Reaction of Functional Groups

In the following exchange reaction, the sugar chain labeled with a hydrazide group-containing compound was reacted with an aminooxy group-containing compound (or a hydrazide group-containing compound), whereby label was transferred by the hydrazone-oxime exchange (or hydrazone-hydrazone exchange). By comparison, as for the sugar chain labeled with an aminooxy group-containing compound, label was also attempted to be transferred. The progress of the reaction was confirmed by MALDI-TOF-MS.

(A) Exchange Reaction of Functional Groups (1) Hydrazone-Hydrazone Exchange Reaction To a solution of the labeled chitotriose-AcWRh (d) of Experimental Example 5(1) was added 10 equivalents of d-AcWRh (e) of Experimental Example 1(A), and the pH was adjusted to 5 with acetic acid. The reaction solution was heated at 90 degree centigrade for 1 hour, and then a part of the reaction solution was taken out and mixed with the labeled chitotriose-aoWR (H) of Experimental Example 5(2) with a known concentration as an internal standard. This resulting mixture was analyzed by MALDI-TOF-MS, and a ratio of the labeled chitotriose-AcWRh (d) contained in the reaction solution to the labeled chitotriose-d-AcWRh (e) obtained in this reaction was calculated.

(2) Hydrazone-Oxime Exchange Reaction

To a solution of the labeled chitotriose-AcWRh (d) of Experimental Example 5(1) was added 10 equivalents of aoWR (H) of Experimental Example 1(B), and the pH was adjusted to 5 with acetic acid. The reaction solution was heated at 90 degree centigrade for 1 hour, and then a part of the reaction solution was taken out and mixed with the labeled chitotriose-aoWR (D) of Experimental Example 5(2) with a known concentration as an internal standard. This resulting mixture was analyzed by MALDI-TOF-MS, and a ratio of the labeled chitotriose-AcWRh (d) contained in the reaction solution to the labeled chitotriose-aoWR (H) obtained in this reaction was calculated.

(3) Oxime-Hydrazone Exchange Reaction

To a solution of the labeled chitotriose-aoWR (H) of Experimental Example 5(2) was added 10 equivalents of AcWRh (d) of Experimental Example 1(A), and the pH was adjusted to 5 with acetic acid. The reaction solution was heated at 90 degree centigrade for 1 hour, and then a part of the reaction solution was taken out and mixed with the labeled chitotriose-d-AcWRh (e) of Experimental Example 5(1) with a known concentration as an internal standard. This resulting mixture was analyzed by MALDI-TOF-MS, and a ratio of the labeled chitotriose-aoWR (H) contained in the reaction solution to the chitotriose-AcWRh (d) obtained in this reaction was calculated.

(4) Oxime-Oxime Exchange Reaction

To a solution of the labeled chitotriose-aoWR (H) of Experimental Example 5(2) was added 10 equivalents of aoWR (D) of Experimental Example 1 (B), and the pH was adjusted to 5 with acetic acid. The reaction solution was heated at 90 degree centigrade for 1 hour, and then a part of the reaction solution was taken out and mixed with the labeled chitotriose-AcWRh (d) of Experimental Example 5(1) with a known concentration as an internal standard. This resulting mixture was analyzed by MALDI-TOF-MS, and a ratio of the chitotriose-aoWR (H) contained in the reaction solution to the chitotriose-aoWR (D) obtained in this reaction was calculated.

(B) Study of Exchange Reaction of Functional Groups

Figure 3:
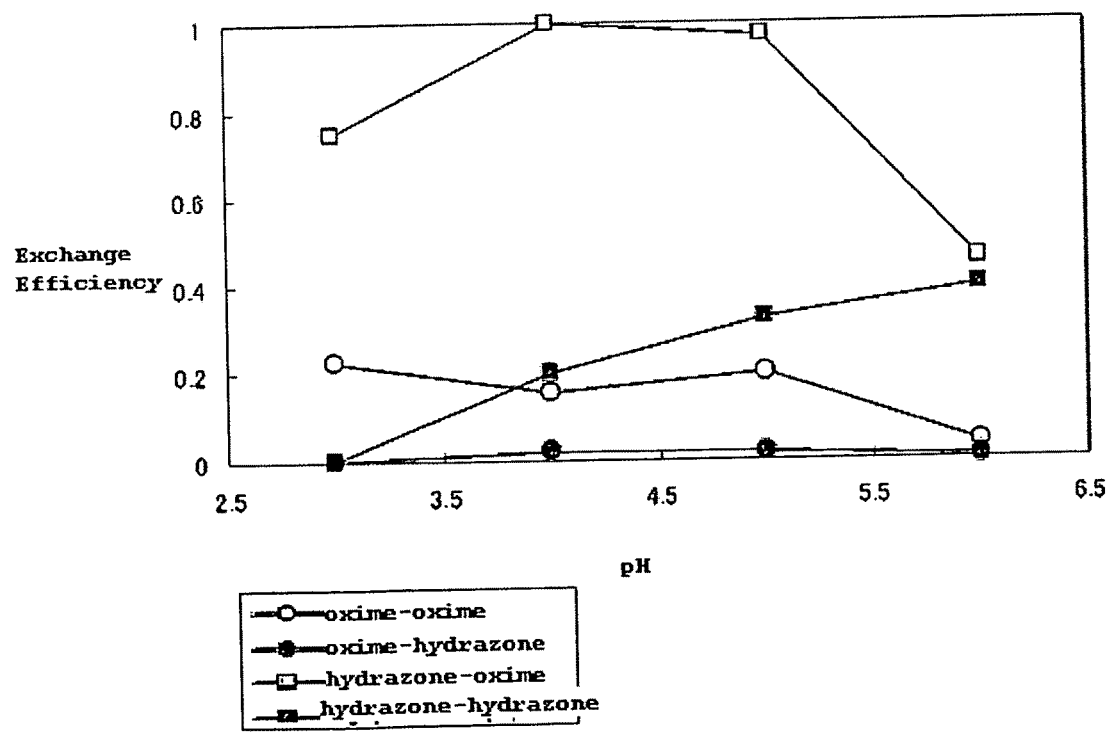
FIG. 3 is a graph illustrating a relationship between the pH and the exchange efficiency of the exchange reaction in the sugar chain release step of the Example. The horizontal axis represents the pH, while the vertical axis represents the exchange efficiency. The exchange from oxime to oxime is indicated as ○, the exchange from oxime to hydrazone is indicated as ●, the exchange from hydrazone to oxime is indicated as □, and the exchange from hydrazone to hydrazone is indicated as ◆.

FIG. 3 is a graph illustrating the yields of the exchange reactions of the above 4 patterns.

It was found that the efficiency of the hydrazone-hydrazone exchange reaction and the hydrazone-oxime exchange reaction was higher than that of the oxime-hydrazone exchange reaction and the oxime-oxime exchange reaction.

That is, the hydrazone bond was easily subjected to the exchange reaction rather than the oxime bond. Furthermore, it was also found that the hydrazone-oxime exchange proceeded with good efficiency rather than the hydrazone-hydrazone exchange.

Experimental Example 7

Exchange Reaction from Solid Phase to Liquid Phase (A) Comparison of Exchange Reaction Efficiency From the results of liquid phase exchange reaction in Experimental Example 6, it was found that the hydrazone-oxime exchange proceeded the most efficiently. As shown below, the efficiency of the exchange reaction from solid phase to liquid phase was also compared in the same manner.

Beads containing a hydrazide group capturing the serum sugar chain in Experimental Example 4 and beads containing an aminooxy group capturing the serum sugar chain in the same manner as in Experimental Example 4 were used for the comparison. To each of sugar chain capturing beads was added 20 μl of aoWR (H) solution (20 mM) or AcWRh (H) solution (20 mM) and further 180 μl of 2% acetic acid/acetonitrile solution, and the resulting mixture was heated at 80 degree centigrade for 45 minutes. After the completion of the reaction, the supernatant was recovered and the MALDI-TOF-MS measurement was carried out.

Figure 4:
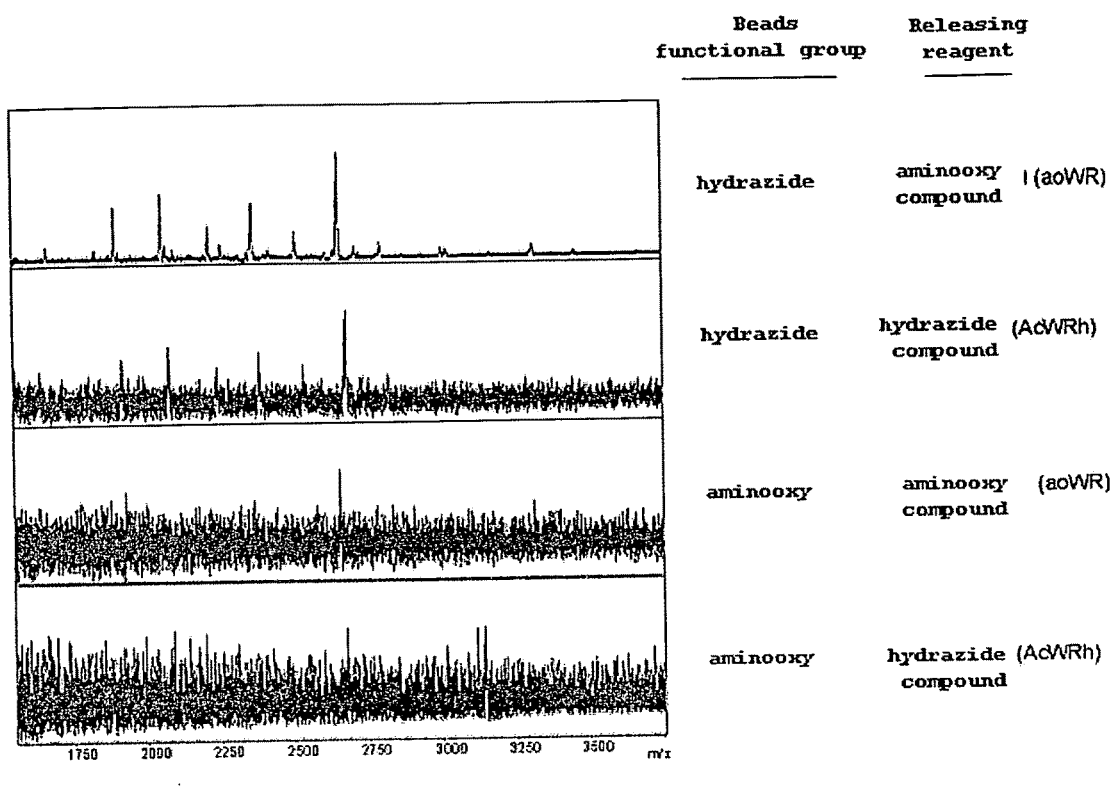
FIG. 4 illustrates a MALDI-TOF-MS chart of the reactant obtained in the exchange reaction of FIG. 3. The horizontal axis represents the molecular weight (m/z), while the vertical axis represents the intensity. From the top of the chart, a functional group of the beads is hydrazide when a releasing reagent is an aminooxy compound (aoWR), a functional group of the beads is hydrazide when a releasing reagent is a hydrazide compound (AcWRh), a functional group of the beads is aminooxy when a releasing reagent is an aminooxy compound (aoWR), and a functional group of the beads is aminooxy, when a releasing reagent is a hydrazide compound (AcWRh) respectively.

FIG. 4 is a MALDI-TOF-MS chart.

As clear from the S/N ratio of the chart, it was found that the efficiency was the best when beads containing a hydrazide group captured the sugar chain and an aminooxy compound released it. This result is consistent with the result from the comparison of the reaction efficiency in the liquid phase in Experimental Example 6.

(B) Re-Release of Sugar Chain from Beads by Exchange Reaction (1) Re-Release of Sugar Chain from Polymer Beads Containing Hydrazide Group To polymer beads containing a hydrazide group bonded to the sugar chain in Experimental Example 4 were added 20 μl of aoWR (H) solution (20 mM) and 180 μl of 2% acetic acid/acetonitrile solution, and the resulting mixture was heated at 80 degree centigrade for 45 minutes. After the completion of the reaction, the supernatant was recovered and an internal standard substance (chitotetraose) was added thereto for carrying out the MALDI-TOF-MS measurement, whereby the amount of the recovered sugar chain was calculated.

(2) Re-Release of Sugar Chain from Commercial Beads (Affi-Gel Hz)

With respect to Affi-Gel Hz capturing the serum sugar chain in the same manner as in Experimental Example 4, the sugar chain was re-released in the same manner as in (1) of Experimental Example 7(B), whereby the amount of the recovered sugar chain was calculated.

Figure 5:
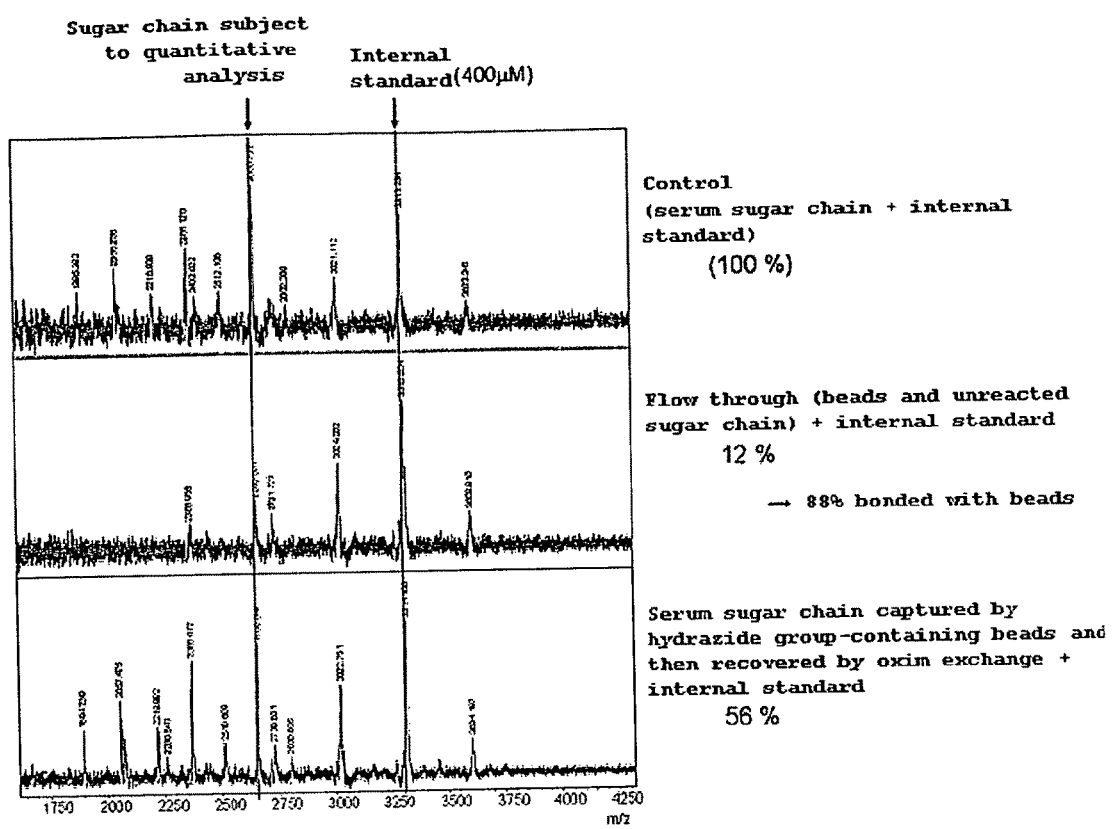
FIG. 5 illustrates a MALDI-TOF-MS chart of the sugar chain recovered in the method of (1) of Experimental Example 7 (B). The horizontal axis represents the molecular weight (m/z), while the vertical axis represents the intensity. The top of the chart indicates control (serum sugar chain+400 µM of internal standard) the middle indicates a flow through sample ((beads and unreacted sugar chain)+400 µM of internal standard), and the bottom indicates a sample (serum sugar chain captured by using beads containing a hydrazide group and then recovered by oxime exchange+400 µM of internal standard). When the intensity of the sugar chain subjected to quantitative analysis of control was taken as 100%, the flow through sample was 12% (88% bonded to beads), while the sample was 56%.

FIG. 5 illustrates a MALDI-TOF-MS chart of the sugar chain recovered in the method of (1) of Experimental Example 7(B).

As a result of the calculation from the signal amount of the internal standard substance, it was found that 56% of the amount of the sugar chain used could be recovered.

Figure 6:
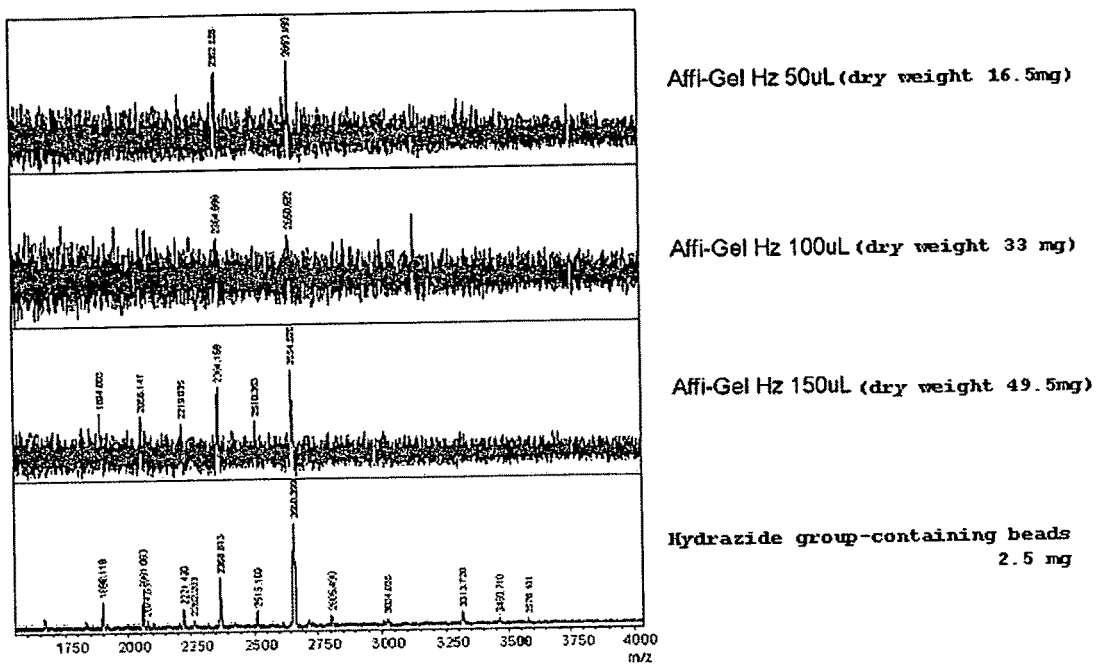
FIG. 6 illustrates a MALDI-TOF-MS chart of the sugar chain recovered in the method of (2) of Experimental Example 7 (B). The horizontal axis represents the molecular weight (m/z), while the vertical axis represents the intensity. The chart indicates the results when, from the top of the chart, 50 µl (dry weight 16.5 mg) of Affi-Gel Hz, 100 µl (dry weight 33 mg) thereof, 150 µl (dry weight 49.5 mg) thereof, and 2.5 mg of beads containing a hydrazide group were used.

FIG. 6 illustrates a MALDI-TOF-MS chart of the sugar chain recovered in the method of (2) of Experimental Example 7 (B). At the same time, the chart of the sugar chain recovered in (1) of Experimental Example 7(B) was also illustrated.

From the S/N ratio of the mass spectrum, it was obviously found that the amount of the recovered sugar chain was small when commercial beads were used. It was found that, even when the amount of beads used was increased by 3 times, it failed to reach the polymer beads containing a hydrazide group by the signal amount. This is considered, as described above, because the amount of the functional group of commercial beads is small (about 1/100) as compared to beads of the present invention.

Experimental Example 8

Exchange Reaction from Liquid Phase to Solid Phase

As illustrated below, the sugar chain labeled with a hydrazide compound (hydrazone bond) was brought into contact with polymer beads containing an aminooxy group, whereby the hydrazone-oxime exchange reaction from liquid phase to solid phase was carried out. This method could be applied such that, for example, the sugar chain was labeled with a fluorescent hydrazide compound, and then the sugar chain was isolated by HPLC or the like and reacted with beads, whereby the isolated sugar chain was immobilized onto beads. In short, this method can be used as a method for randomly selecting a sugar chain from sugar chain mixtures (for example, sugar chain recovered from glycoprotein) and presenting the selected sugar chain onto a surface of the beads. Further, as an application example, a solid phase substrate can also be used instead of beads.

(1) Bonding of Hydrazine Compound (AcWRh (d)) with Sugar Chain

AcWRh (d) of Experimental Example 1 (A) was dissolved in methanol with a concentration of 10 mM. 10 μmol of the sugar chain released from fetuin that was glycoprotein was taken in a vessel. 1 μl of a hydrazide compound solution was added and 100 μl of acetonitrile containing 2% acetic acid was further added. The resulting material was heated at 80 degree centigrade for 45 minutes, whereby the sugar chain and AcWRh (d) were reacted.

(2) Bonding of Hydrazine Compound (d-AcWRh (e)) with Sugar Chain

The sugar chain and d-AcWRh (e) were reacted in the same manner as in Experimental Example 8(1).

(3) Exchange Reaction 5 mg of polymer beads containing an aminooxy group was taken in a vessel, and the sugar chain bonded to AcWRh (d) was put thereinto. The pH was adjusted to 4 with an acetic acid buffer solution, and the resulting solution was reacted at 80 degree centigrade for 1 hour. After the completion of the reaction, the supernatant was recovered, the labeled d-AcWRh (e) sugar chain with a known concentration was added as an internal standard, and the MALDI-TOF-MS measurement was carried out, whereby the amount of the sugar chain (NA3: Asialo, galactosylated triantennary glycan typically paid attention to) was obtained. As the negative control, the system free from polymer beads containing an aminooxy group was treated in the same manner.

Figure 7:
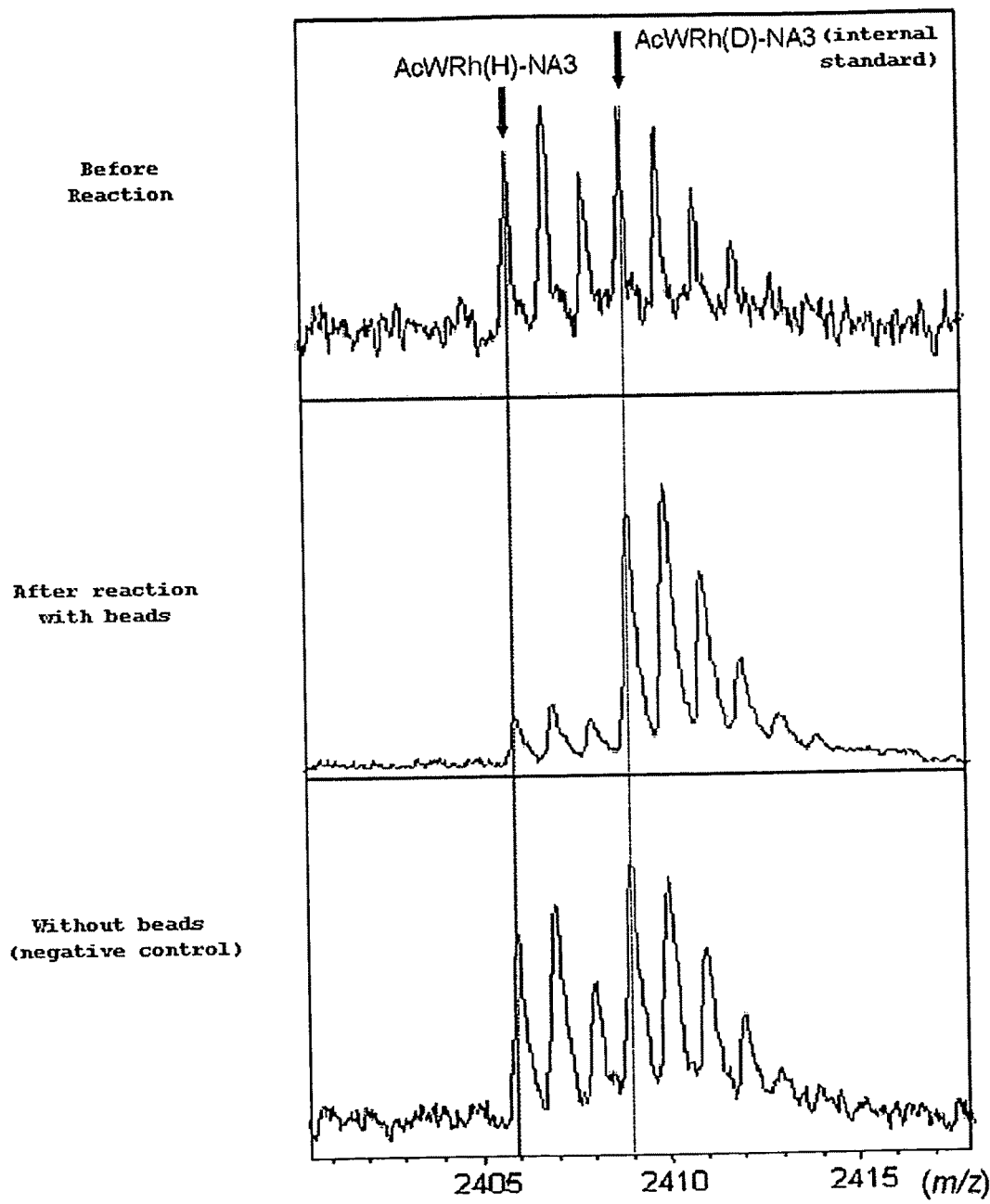
FIG. 7 illustrates a MALDI-TOF-MS chart of the sugar chain recovered in the method of Experimental Example 8(1). The horizontal axis represents the molecular weight (m/z), while the vertical axis represents the intensity. The chart indicates the results in cases of, from the top of the chart, before reaction, after reaction with beads and without using beads (negative control).

FIG. 7 illustrates a MALDI-TOF-MS chart.

In the system in which polymer beads containing an aminooxy group was reacted, about 20% of the amount of the sugar chain was observed. On the other hand, in the negative control, the amount of the sugar chain was hardly changed. From this fact, it was found that about 80% of the amount of the sugar chain was bonded on polymer beads containing an aminooxy group.

Experimental Example 9

Monosaccharide Immobilized Beads

Preparation of Monosaccharide Immobilized Beads 10 mg of polymer beads containing an aminooxy group of Experimental Example 1(B) was taken in a vessel, and 10

μmol of galactose (Gal) or N-acetylglucosamine (GlcNAc) was added thereto. 200 μl of acetonitrile containing 2% acetic acid was added thereto, and the resulting material was heated at 80 degree centigrade for 1 hour, whereby the sugar was immobilized onto beads. Thereafter, beads were sequentially washed with a 0.5% SDS solution, methanol and pure water, whereby foreign matters were removed.

(2) Verification of Lectin Capturing Ability

Three kinds of labeled HRP (horse radish peroxidase) lectins: HRP-Concanavalin A (Con A), HRP-Wheat germ agglutinin (WGA) and HRP-*Ricinus communis* agglutinin (RCA120) (all lectins manufactured by Seikagaku Corporation) were respectively dissolved to the concentration of 1 μg/ml in a binding buffer (50 mM Tris/HCl, 100 mM NaCl, 10 mM CaCl2, 10 mM MgCl2, pH 7.6). 1 mg of beads onto which monosaccharide was immobilized in Experimental Example 9(1) was taken in a vessel, and 100 μl of any of lectin solutions was added thereto, and the resulting mixture was mildly stirred at 37 degree centigrade for 16 hours. Thereafter, beads were washed with a binding buffer containing 0.05% of Tween-20 and a binding buffer respectively for 1 hour. Labeled HRP lectin bonded on beads was the development of the color with a peroxidase coloring kit (a product of Sumitomo Bakelite Co., Ltd.) for measuring the absorbance of the solution at 450 nm, whereby the binding amount of lectin was estimated.

As shown in FIG. 8, it was found that lots of WGA was bonded to GlcNAc immobilized beads, while lots of RCA120 was bonded to Gal immobilized beads. It has been known that WGA mainly recognized GlcNAc, while RCA120 mainly recognized Gal. Monosaccharide immobilized beads obtained by applying the method of the present invention could surely recognize and capture corresponding lectin.

Experimental Example 10

Oligosaccharide Immobilized Beads

Preparation of Oligosaccharide Immobilized Beads 10 mg of polymer beads containing an aminooxy group of Experimental Example 1(B) was taken in a vessel, 1 μmol of the fetuin sugar chain of Experimental Example 2(1) or a ribonuclease B sugar chain solution was added in terms of the amount of the sugar chain. 200 μl of acetonitrile containing 2% acetic acid was added and the resulting material was heated at 80 degree centigrade for 1 hour, whereby the sugar chain was immobilized onto beads. Thereafter, beads were sequentially washed with a 0.5% SDS solution, methanol and pure water, whereby foreign matters were removed.

(2) Verification of Lectin Capturing Ability

Capture of Concanavalin A (Con A)

1 mg of beads with Ribonuclease B sugar chain immobilized thereon in Experimental Example 10(1) was taken in a vessel. 1 μl of the Con A solution (10 μg/ml) and 100 μl of the binding buffer were added thereto, and the resulting material was mildly stirred at 37 degree centigrade for 16 hours, whereby Con A was bonded to the sugar chain on beads. Thereafter, beads were washed with a binding buffer containing 0.05% of Tween-20 and a binding buffer respectively for 1 hour. The cleaning solution was removed, 20 μl of 0.5 M methyl-a-mannopyranoside was added as hapten, and the resulting mixture was stirred at 37 degree centigrade for 2 hours, whereby Con A bonded to the sugar chain on beads was released. The supernatant was recovered, a trypsin solution (sequence grade trypsin, a product of Promega) was added, the reaction mixture was allowed to stand at 37 degree centi-grade for 16 hours, and the released Con A was fragmented into peptides. A part of the reaction solution was taken and the MALDI-TOF-MS measurement was carried out. As shown below, data was compared with already known amino acid sequence of Con A.

(1) The trypsin cut position was presumed from the amino acid sequence of Con A (already known) for estimating the mass number of a peptide fragment. Further, it was compared with the measured mass spectrum data so that it was confirmed that they were consistent. At this time, the mass number of the peptide fragment was estimated using PeptideMass (a tool published on web).

(2) MS/MS analysis of the representative spectrum of the obtained spectra was carried out. As a result of the analysis using MASCOT MS/MS Ion Search (a tool for estimating original protein from MS/MS data of the peptide fragment), it was confirmed that the peptide was surely derived from Con A.

As shown in FIG. 9, lots of peaks were detected, in which the Con A-derived peptide and the mass number were consistent. The main sugar chain contained in Ribonuclease B was a high mannose-type sugar chain (lots of mannose residues contained), while Con A has a property of recognizing mannose and binding to it. From these facts, Con A could be recognized and captured by the sugar chain immobilized onto beads.

The invention claimed is:

1. A method for preparing a sample in which polymer beads A containing a hydrazine group and having a crosslinked polymer structure represented by the following formula (4) is bonded to a sugar chain and/or a sugar derivative via hydrazone formation between the hydrazine group of the polymer beads A and the reducing end of the sugar chain and/or the sugar derivative,

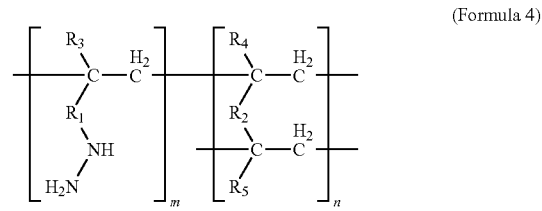

(Formula 4)

wherein, in the formula, $R_1$ and $R_2$ represent a hydrocarbon chain having 1 to 20 carbon atoms which may be interrupted with —O—, —S—, —NH—, —CO— or —CONH—; $R_3$, $R_4$ and $R_5$ represent H, $CH_3$ or a hydrocarbon chain having 2 to 5 carbon atoms; and m and n represent the number of monomer units and wherein said polymer beads A having a hydrazine group and said hydrazine group has a thy weight of not less than 100 nmol per 1 mg.

2. The method for preparing a sample as set forth in claim 1, in which said polymer beads A has a erosslinked polymer structure represented by the following formula (5),

[Chemical Formula 5]

(Formula 5)

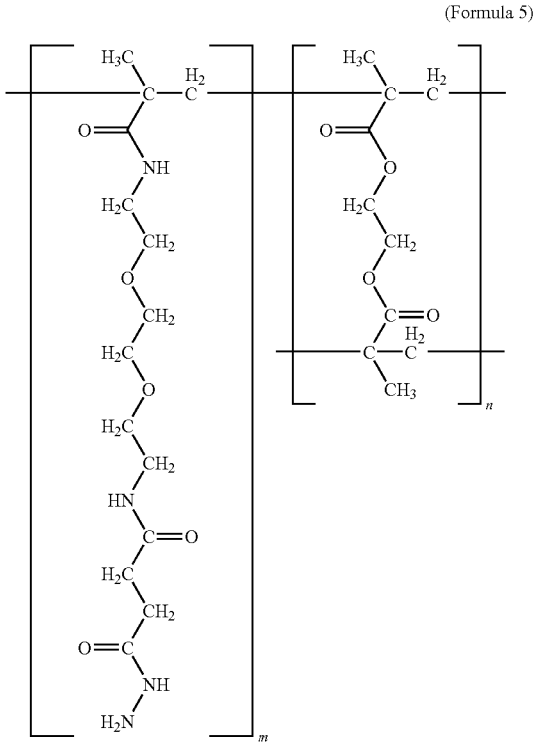

wherein, in the formula, m and n represent the number of monomer units.

3. The method for preparing a sample as set forth in claim 1, in which said polymer beads A is a polymer particle having an average particle diameter of equal to or more than 0.1 and equal to or less than 500 μm.

4. The method for preparing a sample as set forth in claim 1, in which said polymer beads A is stable at the pH of 3 to 8.

5. The method for preparing a sample as set forth in claim 1, in which said polymer beads A is stable under pressure of at least not more than 1 MPa.

6. A method for preparing a sample which involves the sugar chain capture step comprising binding polymer beads A to a sugar chain and/or a sugar derivative according to the method for preparing a sample as set forth in claim 1, and
the sugar chain release step comprising the action of a substance B containing an aminooxy group or a hydrazide group on a complex of the polymer beads A and the sugar chain and/or the sugar derivative, captured in the sugar chain capture step, and binding said sugar chain and/or said sugar derivative while cut off from said polymer heads A to said substance B in accordance with the hydrazone-oxime exchange reaction or hydrazone-hydrazone exchange reaction occurred between said complex and said substance B.

7. The method for preparing a sample as set forth in claim 6, in which said substance B comprises a moiety containing chromophore or fluorophore.

8. The method for preparing a sample as set forth in claim 6, in which said substance B is a substance selected from the group consisting of the following substances containing a hydrazide group 5-Dimethylaminonaphthalene-1-sulfonyl hydrazine (Dansylhydrazine); 2-hydrazinopyridine; 9-fluorenylmethyl carbazate (Fmoc hydrazine); benzylhydrazine; 4,4-dffluoro-5,7-dimethyl-4-bora-3a,4a-diaza-s-indacene-3-propionoc acid, hydrazide; 2-(6,8-difluoro-7-hydroxy-4-methylcoumarin)acetohydrazide; 7-diethylaminocoumarin-3-carboxylic acid, hydrazide (DCCH); phenylhydrazine; 1-Naphthaleneacethydrazide; 2-hydrazinobenzoic acid; and phenylacetic hydrazide; or the following substances containing an aminooxy group or a salt, of O-benzylhydroxylamine; O-phenylhydroxylamine; O-(2,3,4,5,6-pentafluorobenzl)hydroxylamine; O-(4-nitrobenzyl)hydroxylamine; 2-aminooxypyridine; 2-aminooxymethylpyridine; 4-[(aminooxyacetyl)amino]benzoic acid methyl ester; 4-[(aminooxyacetyl)amino]benzoic acid ethyl ester; and 4-[(aminooxyacety)amino]benzoic acid n-butyl ester.

9. The method for preparing a sample as set forth in claim 6, in which said substance B comprises a moiety consisting of at least one of an arginine residue, a tryptophan residue, a phenylalanine residue, a tyrosine residue, a cysteine residue and a derivative thereof.

10. The method for preparing a sample as set forth in claim 6, in which said substance B has a structure represented by the following formula (7),

[Chemical Formula 6]

wherein, in the structural formula, R represents $-CH_3$ or $-CD_3$.

11. A method for preparing a sample in which a hydrazone bond between polymer beads A and a sugar chain and/or a sugar derivative is dissociated and the sugar chain and/or sugar derivative released by treating the polymer heads A under acidic conditions to, the polymer beads A having a structure represented by the following formula (4),

[Chemical Formula 11]

wherein, in the formula, $R_1$ and $R_2$ represent a hydrocarbon chain having 1 to 20 carbon atoms which may he interrupted with —O—, —S—, —NH—, —CO— or —CONH—; $R_3$, $R_4$ and $R_5$ represent H, $CH_3$ or a hydrocarbon chain having 2 to 5 carbon atoms; and m and n represent the number of monomer units, and
wherein the polymer beads A have a hydrazine group of a dry weight of not less than 100 nmol per 1 mg.

12. The method for preparing a sample as set forth in claim 1, in which in the formula, $R_3$, $R_4$ and $R_5$ represent $CH_3$ or a hydrocarbon chain having 2 to 5 carbon atoms.

13. The method for preparing a sample as set forth in claim 11, in which said polymer beads A has a crosslinked polymer structure represented by the following formula (5),

[Chemical Formula 20]

wherein, in the formula, m and n represent the number of monomer units.

* * * * *